United States Patent
Adams et al.

(10) Patent No.: US 9,943,266 B2
(45) Date of Patent: Apr. 17, 2018

(54) TIME-DOMAIN INTERFERENCE REMOVAL FOR HEART RATE MEASUREMENTS

(71) Applicant: ANALOG DEVICES, INC., Norwood, MA (US)

(72) Inventors: Robert Adams, Acton, MA (US); Sefa Demirtas, Malden, MA (US); Jeffrey G. Bernstein, Middleton, MA (US)

(73) Assignee: ANALOG DEVICES, INC., Norwood, MA (US)

(*) Notice: Subject to any disclaimer, the term of this patent is extended or adjusted under 35 U.S.C. 154(b) by 88 days.

(21) Appl. No.: 14/972,368

(22) Filed: Dec. 17, 2015

(65) Prior Publication Data
US 2016/0317096 A1 Nov. 3, 2016

Related U.S. Application Data

(60) Provisional application No. 62/170,339, filed on Jun. 3, 2015, provisional application No. 62/154,688, filed on Apr. 29, 2015.

(51) Int. Cl.
*A61B 5/02* (2006.01)
*A61B 5/00* (2006.01)
(Continued)

(52) U.S. Cl.
CPC .......... *A61B 5/721* (2013.01); *A61B 5/02416* (2013.01); *A61B 5/02438* (2013.01);
(Continued)

(58) Field of Classification Search
CPC . A61B 5/721; A61B 5/02416; A61B 5/02438; A61B 5/725; A61B 5/7275; A61B 5/11; A61B 2562/0219; A61B 2562/0233
(Continued)

(56) References Cited

U.S. PATENT DOCUMENTS 5,423,325 A 6/1995 Burton
5,816,122 A * 10/1998 Benning ................. F16F 15/02
 408/11
(Continued)

FOREIGN PATENT DOCUMENTS

WO 2012/073069 6/2012
WO 2016/176067 11/2016

OTHER PUBLICATIONS

International Search Report and Written Opinion issued in International Patent Application Serial No. PCT/US2016/028034 dated Aug. 14, 2016, 17 pages.
(Continued)

*Primary Examiner* — Michael Carey
(74) *Attorney, Agent, or Firm* — Patent Capital Group

(57) ABSTRACT

Heart rate monitors are plagued by noisy photoplethysmography (PPG) data, which makes it difficult for the monitors to output a consistently accurate heart rate reading. Noise is often caused by motion. Using known methods for processing accelerometer readings that measure movement to filter out some of this noise may help, but not always. The present disclosure describes an improved front-end technique (time-domain interference removal) based on using adaptive linear prediction on accelerometer data to generate filters for filtering the PPG signal prior to tracking the frequency of the heartbeat (heart rate). The present disclosure also describes an improved back-end technique based on steering the frequency of a resonant filter in order to track the heartbeat. Implementing one or both of these techniques leads to more accurate heart rate measurements.

19 Claims, 20 Drawing Sheets

(51) Int. Cl.
*A61B 5/024* (2006.01)
*A61B 5/11* (2006.01)

(52) U.S. Cl.
CPC ............ *A61B 5/725* (2013.01); *A61B 5/7275* (2013.01); *A61B 5/11* (2013.01); *A61B 2562/0219* (2013.01); *A61B 2562/0233* (2013.01)

(58) Field of Classification Search
USPC ................ 600/508, 509, 516, 517, 519, 527
See application file for complete search history.

(56) References Cited

U.S. PATENT DOCUMENTS

| | | | |
|---|---|---|---|
| 2004/0071206 A1* | 4/2004 | Takatsu | H03H 21/0012 375/232 |
| 2008/0013747 A1 | 1/2008 | Tran | |
| 2014/0018635 A1 | 1/2014 | Buchheim et al. | |
| 2014/0275852 A1 | 9/2014 | Hong et al. | |
| 2014/0275854 A1 | 9/2014 | Venkatraman et al. | |
| 2014/0288438 A1* | 9/2014 | Venkatraman | A61B 5/721 600/483 |
| 2016/0015280 A1 | 1/2016 | Hyde et al. | |
| 2016/0317097 A1 | 11/2016 | Adams et al. | |

OTHER PUBLICATIONS

H. Harry Asada, *Active Noise Cancellation Using MEMS Accelerometers for Motion-Tolerant Wearable Bio-Sensors*, Proceedings of the 26th Annual International Conference of the IEEE EMBS, San Francisco, CA, USA, Sep. 1-5, 2004, 4 pages.

Gary Comtois et al., *A Comparative Evaluation of Adaptive Noise Cancellation Algorithms for Minimizing Artifacts in a Forehead-Mounted Wearable Pulse Oximeter*, Proceedings of the 29th Annual International Conference of the IEEE EMBS, Lyon, France, Aug. 23-26, 2007, 4 pages.

Hayato Fukushima et al., *Estimating Heart Rate Using Wrist-Type Photoplethysmography and Acceleration Sensor While Running*, 34th Annual International Conference of the IEEE EMBS, San Diego, CA, USA, Aug. 28-Sep. 1, 2012, 4 pages.

Hyonyoung Han et al., *Development of Real-Time Motion Artifact Reduction Algorithm for A Wearable Photoplethysmography*, Proceedings of the 29th Annual International Conference of the IEEE EMBS, Lyon, France, Aug. 23-26, 2007, 4 pages.

Non-Final Office Action (OA1) issued in U.S. Appl. No. 14/972,447 dated Jul. 11, 2017, 22 pages.

Ewelina Nowak et al., *Robust Real-Time PPG-Based Heart Rate Monitoring*, Gdansk University of Technology, Gdansk, 978-0-9928626-3-3/15 © 2015 IEEE, 5 pages.

Gary W. Comtois, *Implementation of Accelerometer-Based Adaptive Noise Cancellation in a Wireless Wearable Pulse Oximeter Platform for Remote Physiological Monitoring and Triage*, A Thesis, Worcester Polytechnic Institute, Aug. 31, 2007, 149 pages.

Tim Schack et al., *A New Method for Heart Rate Monitoring During Physical Exercise Using Photoplethysmographic Signals*, Signal Processing Group, 978-0-9928626-3-3/15 © 2015 IEEE.

Abdullah Alzahrani et al., *A Comparative Study of Physiological Monitoring with a Wearable Opto-Electronic Patch Sensor (OEPS) for Motion Reduction*, Biosensors 2015, 5, 288-307; doi: 10-3390/bios5020288, ISSN 2079-6374, www.mdpi.com/journal/biosensors, 20 pages.

Samira Jaafari, *Adaptive Filtering for Heart Rate Signals*, San Jose State University, SJSU ScholarWorks, Master's Thesis and Graduate Research, 2014, 97 pages.

Zhilin Zhang, *Photoplethysmography-Based Heart Rate Monitoring in Physical Activities via Joint Sparse Spectrum Reconstruction*, IEEE Transactions on Biomedical Engineering vol. 62, No. 8, Aug. 2015, 9 pages.

Rasoul Yousefi et al., *A Motion-Tolerant Adaptive Algorithm for Wearable Photoplethysmographic Biosensors*, IEEE Journal of Biomedical and Health Informatics, Mar. 2014, 13 pages.

Rousel Yousefi et al., *Adaptive Cancellation of Motion Artifact in Wearable Biosensors*, 34th Annual International Conference of the IEEE EMBS, San Diego, CA, USA, Aug. 28-Sep. 1, 2012, 978-1-4577-1787-1/12 © 2012, IEEE, 5 pages.

\* cited by examiner

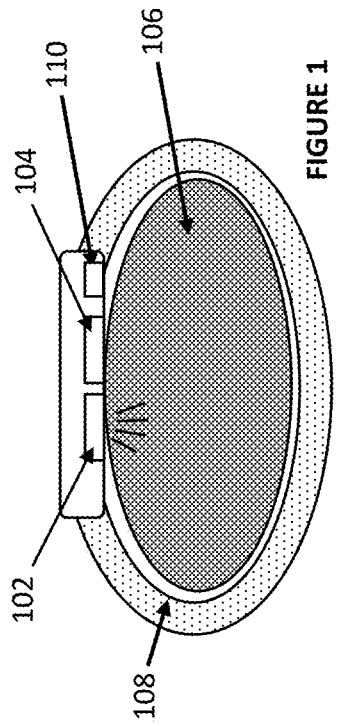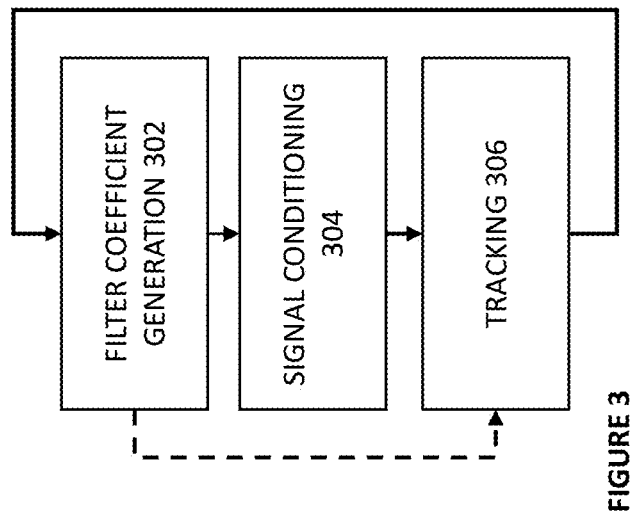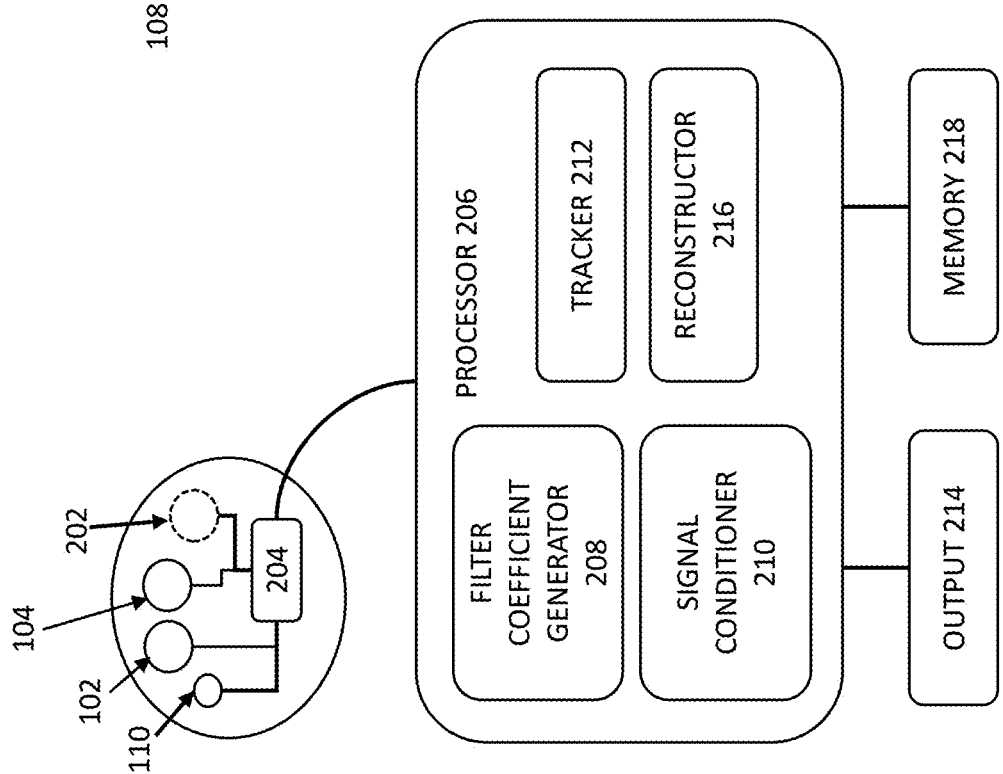

TIME-DOMAIN INTERFERENCE REMOVAL FOR HEART RATE MEASUREMENTS

CROSS-REFERENCE TO RELATED APPLICATIONS

This application claims the benefit of and priority from U.S. Provisional Patent Application Ser. No. 62/154,688 filed 29 Apr. 2015 entitled "SYSTEMS AND METHODS FOR HEART RATE MEASUREMENT" and from U.S. Provisional Patent Application Ser. No. 62/170,339 filed 3 Jun. 2015 entitled "TIME-DOMAIN INTERFERENCE REMOVAL AND IMPROVED TRACKING MECHANISM FOR HEART RATE MEASUREMENTS", each of which is incorporated herein by reference in its entirety.

TECHNICAL FIELD OF THE DISCLOSURE

The present disclosure relates to the field of digital signal processing, in particular to digital signal processing for tracking a heartbeat frequency in a noisy environment.

BACKGROUND

Modern electronics are ubiquitous in healthcare. For example, monitoring devices often include electronic components and algorithms to sense, measure, and monitor living beings. Monitoring equipment can measure vital signs such as respiration rate, oxygen level in the blood, heart rate, and so on. Not only are monitoring devices used in the clinical setting, monitoring devices are also used often in sports equipment and consumer electronics.

One important measurement performed by many of the monitoring equipment is heart rate, typically measured in beats per minute (BPM). Athletes use heart rate monitors to get immediate feedback on a workout, while health care professionals use heart rate monitors to monitor the health of a patient. Many solutions for measuring heart rate are available on the market today. For instance, electronic heart rate monitors can be found in the form of chest straps and watches. However, these electronic heart rate monitors are often not very accurate, due to a high amount of noise present in the signals provided by the sensors of these monitors. The noise is often caused by the fact that the user is moving and also by the lack of secure contact between the monitor and the user. This noisy environment often leads to an irregular, inaccurate or even missing readout of the heart rate.

Overview

Heart rate monitors are plagued by noisy photoplethysmography (PPG) data, which makes it difficult for the monitors to output a consistently accurate heart rate reading. Noise is often caused by motion. Using known methods for processing accelerometer readings that measure movement to filter out some of this noise may help, but not always. The present disclosure describes an improved front-end technique (time-domain interference removal) based on using adaptive linear prediction on accelerometer data to generate filters for filtering the PPG signal prior to tracking the frequency of the heartbeat (heart rate). The present disclosure also describes an improved back-end technique based on steering the frequency of a resonant filter in order to track the heartbeat. Implementing one or both of these techniques leads to more accurate heart rate measurements.

According to an improved front-end technique, a method for assisting identification and/or tracking of a frequency of a heartbeat signal present in one or more first signals generated by one or more sensors in a noisy environment is disclosed. The method includes steps of a) receiving data samples of a first signal; b) receiving data samples of a second signal indicative of motion of the one or more sensors; c) applying adaptive linear prediction to at least a portion of the data samples of the second signal to determine coefficients of an adaptive linear filter configured to filter (i.e., substantially attenuate) at least a part of noise content present in the second signal from a signal indicative of the motion of the one or more sensors; and d) generating a filtered first signal by subtracting from the first signal a signal generated by applying a filter comprising the determined coefficients to the first signal (In other words, the first signal is filtered based on processing the data samples of the first signal with a filter comprising the determined coefficients, where the step of filtering the first signal substantially attenuates signal content corresponding to the motion of the one or more sensors).

According to an improved back-end technique, a method for extracting a frequency of a heartbeat signal present within an input signal generated by one or more sensors using a structure implementing a first filter ($FILTER_A$) and a second filter ($FILTER_B$) is disclosed. In some embodiments, the structure may be configured to implement the first and second filters as a separate filters comprising their respective, different, components. In other embodiments, the structure may be a resource-shared structure where at least some, but possibly all, of the components used in implementing the first filter are also used (i.e. shared) in implementing the second filter, and vice versa. Regardless of this, the first filter and the second filter are filters have a frequency $F\_RES$ at which the amplitudes of their outputs are substantially equal and for which, above the frequency $F\_RES$, the amplitude of the first filter becomes larger than the amplitude of the second filter, and, below the frequency $F\_RES$, the amplitude of the second filter becomes larger than the amplitude of the first filter. The method includes steps of: a) determining an amplitude (A) of an output generated by the first filter in response to the first filter receiving the input signal and one or more filter control parameters; b) determining an amplitude (B) of an output generated by the second filter in response to the second filter receiving the input signal and the one or more filter control parameters; c) updating the filter control parameters based on the amplitudes A and B and proceeding to step a); d) determining the frequency of the heartbeat signal based on the one or more filter control parameters.

BRIEF DESCRIPTION OF THE DRAWING

To provide a more complete understanding of the present disclosure and features and advantages thereof, reference is made to the following description, taken in conjunction with the accompanying figures, wherein like reference numerals represent like parts, in which:

FIG. 1 shows an illustrative heart rate monitoring apparatus and a portion of a living being adjacent to the heart rate monitor, according to some embodiments of the disclosure.

FIG. 2 illustrate a system view of a heart rate monitoring apparatus, according to some embodiments of the disclosure;

FIG. 3 illustrates an exemplary flow diagram of a method for tracking a heartbeat frequency present in one or more input signals provided by one or more sensors in a noisy environment, according to some embodiments of the disclosure;

DESCRIPTION OF EXAMPLE EMBODIMENTS OF THE DISCLOSURE

Figure 4:
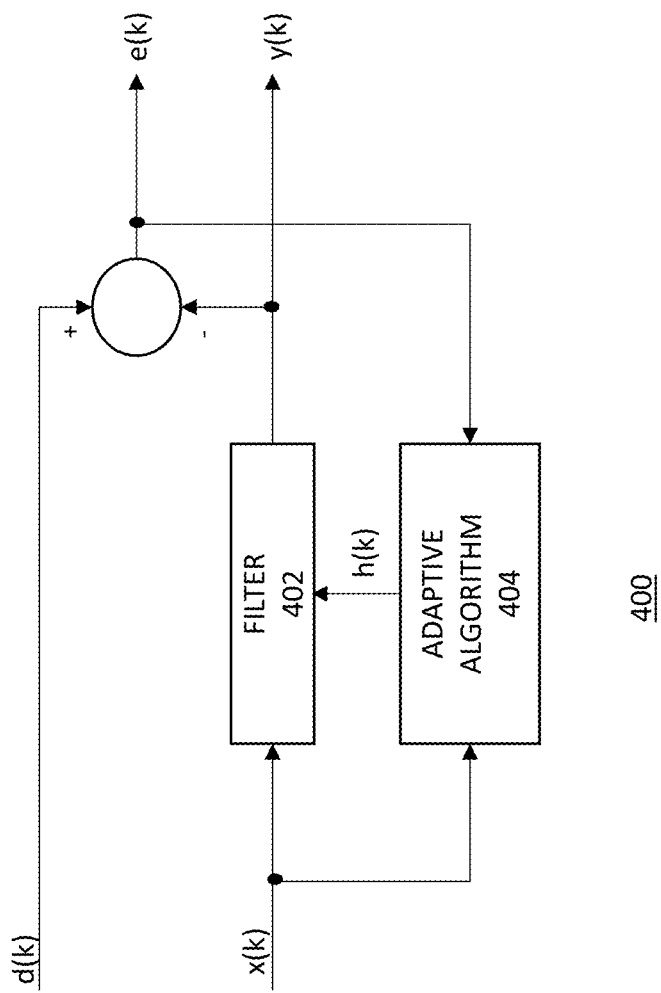
FIG. 4 illustrates an exemplary adaptive filter, according to some embodiments of the disclosure.

Improvements with Respect to Both Front-End and Back-End of Heart Rate Monitors

The present disclosure describes some specific challenges faced by heart rate monitors using a light source and an optical sensor to measure a heart rate of a living being. To address at least some of these challenges, the present disclosure provides two different mechanisms. The first mechanism provides an improved filtering technique for filtering the input signal generated by the optical sensor, referred to herein as a "time-domain interference removal." Since such a mechanism is typically implemented as a part of what may be considered the "front-end" of a heart rate monitor, it is sometimes referred to herein as "front-end processing." The second mechanism described herein provides an improved tracking technique for actually tracking the heart rate using the input signal from the optical sensor. Since the second mechanism is typically implemented as a part of what may be considered "back-end" of a heart rate monitor, it is sometimes referred to herein as "back-end processing."

The improved mechanisms for the front-end and back-end processing described herein are independent from one another, in a sense that implementation of the first mechanism does not necessarily require implementation of the second mechanism, and vice versa. Thus, the first mechanism may be combined with any other tracking mechanism as is known in the art and the second mechanism may be combined with any other signal conditioning mechanism as is known in the art, or the second mechanism may be implemented to track the heart rate directly from the unprocessed (raw) data as acquired by the sensors. Implementing even only one of the two mechanisms described herein leads to more accurate heart rate measurements. Therefore, while systems and methods described herein are sometimes described in context of implementing both mechanisms in order to provide a complete picture of an improved heart monitoring apparatus, embodiments of the present disclosure are not limited to implementing both the first and second mechanisms simultaneously. For example, as will become clear from the explanations provided below, the filter generation and signal conditioning components illustrated in FIGS. 2 and 3 and relevant to the front-end processing in accordance with the improved filtering mechanism described herein are not needed for the functionality of the tracking component illustrated in these figures and relevant to the back-end processing, and vice versa. Consequently, the systems and methods for implementing one of these mechanisms do not have to include components for implementing another one of the mechanisms described herein even though the description of both mechanisms may refer to the same system (such as e.g. illustrated in FIG. 2).

Understanding Issues of Noisy Environment of Heart Rate Monitors

Heart rate monitors are often in direct contact with the skin of a living being. The monitors passively track or measure heart rate by sensing one or more aspects of the skin adjacent to the heart rate monitor. Due to the passive nature of such measurements, the sensor data can be affected by many sources of noise which severely affects the ability of the heart rate monitor to determine an accurate heartbeat. These sources of noise can include external interference to the sensor, internal noise of the sensor and/or heart rate monitor, motion causing disruptions in the sensor's capability in measuring the aspects of the skin, etc. Furthermore, heart rate monitors are affected by variability in the skin of different living beings and the variability of the skin and environment during the use of the heart rate monitor. All these different sources and issues have adverse impact on the heart rate monitor's ability to extract an accurate heart rate.

FIG. 1 shows an illustrative heart rate monitoring apparatus and a portion of a living being adjacent to the heart rate monitor, according to some embodiments of the disclosure. In particular, the FIGURE shows a cross section to illustrate the monitoring apparatus's spatial relationship with the portion of the living being. In this exemplary heart rate monitoring setup, a method of photoplethysmography (PPG) is used, where the heart rate is measured passively or indirectly based on changes in light absorption in the skin as blood is pushed through the arteries. Changes in blood volume as blood is pumped through the arteries results in a variation in the amount of received light, which is translated into electrical pulses by an optical sensor. The pulses in the signal can then be used in extracting a heart rate.

Heart rate monitoring apparatus described herein are not limited to the particular example shown in FIG. 1. Although the disclosure does not describe other types of heart rate monitors in detail, one skilled in the art would appreciate that these challenges are also applicable in other types of heart rate monitors or other types of devices providing heart rate monitoring functions, or even devices utilizing other types of sensing mechanism. Furthermore, the continued process of measuring, following, extracting, determining, or sensing the heart rate (or some other slow varying frequency) over time is referred to as "tracking a slow varying frequency", within the context of the disclosure.

Specifically, FIG. 1 illustrates an exemplary heart rate monitoring apparatus having a light source 102 and an optical sensor 104. The light source can emit light within a range of wavelengths suitable for the application. In some embodiments, the light source 102 and the optical sensor 102 can be provided separately, or a light source 102 can be biased to function as an optical sensor 104. For instance, a red LED can be used as a red light source and a red optical detector. In some embodiments, both the light source 103 and optical sensor 104 can be provided nearby each other in a housing or member of the heart rate monitoring apparatus or in any suitable configuration where the optical sensor 104 can measure absorption of light (as generated by the light source 103) by the part 106 of the living being. The light source shines a light onto a part 106 of a living being 106 and the optical sensor 104 measures light incident onto the optical sensor 104, which can include light being reflected from the part 106 as well as ambient light. Various parts of the living being can be used as part 106, e.g., a finger, an arm, a forehead, an ear, chest, a leg, a toe, etc., as long as changes in the volume of blood can be measured relatively easily. The part 106 can in some cases be internal to the body of the living being.

Generally speaking, if the heart rate monitoring apparatus can be affixed to the part 106 of the living being securely and maintain relatively stable contact with the part 106 during use, the input signal provided by the optical sensor would exhibit very little noise and the heart rate can be easily extracted. However, in many scenarios, the heart rate monitoring apparatus is not securely affixed to the part 106 (even with the use of part 108 involving a band, a strap, adhesive, or other suitable attachments), or having the apparatus securely adhered or attached to the part 106 is not desirable or comfortable for the living being. In these scenarios, the signal provided by the optical sensor 104 is usually affected by noise from ambient light, artifacts caused by motion of the heart rate monitoring apparatus, or by some other noise source. As a result, correctly detecting the heart rate in these non-ideal scenarios, i.e., in a noisy environment, can be challenging. Attempting to detect the heart rate based on a noisy signal can result in irregular or erroneous heart rate readings.

To address this issue, some heart rate monitoring apparatuses include a mechanism which discards certain portions of data if the data is deemed unusable for tracking the heart rate. The mechanism can include an accelerometer 110 to measure the motion of the apparatus to assess whether the input signal is likely to be too degraded by motion artifacts to be relied upon for heart rate determination. In those cases, the accelerometer reading can cause the apparatus to discard data or freeze the heart-rate readout when the accelerometer 110 senses too much motion. Another approach may be to use the accelerometer data to estimate the heart rate based on an estimate of the predicted level of exercise. This can be problematic for heart rate monitoring apparatuses which experiences a large amount of acceleration (e.g., in a sports setting), in which case the heart rate output may be either missing entirely or very inaccurate for a substantial amount of time during use.

Some heart rate monitoring apparatuses discard portions of the signal which are deemed too noisy by assessing signal quality (e.g., how clear spectral peaks are in the frequency domain). This can be helpful in removing noisy portions of the signal, but the data which is not discarded is not always reliable for heartbeat tracking. While such apparatuses can discard a portion of the signal that is too noisy, certain portions of the input signal exhibiting clear spectral peaks can still result in erroneous heartbeat readings because the spectral peaks could have been a result of periodic motion artifacts or other sources of artifacts affecting heart rate detection. For instance, a portion of the input signal degraded by motion artifacts but having clear spectral peaks could cause a heart rate tracking mechanism to lock onto a frequency corresponding to the motion artifact and not to the true heart rate.

Front-End Processing: Overview of an Improved Filtering Mechanism

The aforementioned problems of heart rate monitoring apparatuses stem from having a coarse mechanism for discarding input data, where, as used herein, the term "input data" (and variations thereof, such as e.g. "input signal") refers to data from which a slowly varying frequency, e.g. a heart rate, may be obtained. The present disclosure describes an improved front-end processing mechanism that alleviates some of the issues mentioned above. The improved mechanism is a filtering mechanism that allows for a more nuanced processing of the raw input signal and can enable the input signal to be conditioned in such a way as to allow the tracker to track the heart rate even when the signal was acquired in a noisy setting. By improving on the filtering mechanism, the heart rate monitoring apparatus can achieve more robust performance in a noisy environment. An improved filtering mechanism can increase the amount of the usable data and thereby increase the accuracy and consistency of the heart rate output. Furthermore, the improved filtering mechanism can improve the accuracy of the tracking mechanism for tracking the heartbeat by way of providing a better and more usable input signal.

The improved filtering mechanism is based on recognition that, when a sensor, or multiple sensors, configured to generate an input signal from which the heart rate is to be tracked (such sensor or a plurality of sensors referred to in the following as a "heart rate sensor") are moving (e.g. because a person wearing such heart rate monitoring apparatus is running), their measurements are affected by the movement in a predictable manner. Therefore, if the pattern of motion is known, then it may be possible to identify contributions to the input signal that are attributable to the motion of the heart rate sensor (i.e., motion-related artifact in the input signal) and filter those contributions out. The improved filtering mechanism leverages an insight that, provided that a heart rate sensor is in relatively close proximity to an accelerometer so that both the accelerometer and the heart rate sensor experience the same motion, accelerometer measurements taken at the same time as the measurements by the heart rate sensor may be considered to accurately represent motion of the heart rate sensor when the input signal was acquired. In turn, accelerometer data related to the motion of the heart rate sensor may be used in reducing the amount of noise in the input signal generated by the sensor by identifying motion-related artifacts in the input signal. In particular, using adaptive linear prediction on the accelerometer data allows creating a filter that reduces or eliminates motion-related artifacts from the input signal acquired by the heart rate sensor. As a result, identification/tracking of the heartbeat signal from a noisy sensor signal is improved.

The resulting filtering mechanism is able to better filter the input signal and improve the accuracy of heart rate tracking. The following passages describe in further detail how the improved filtering mechanism can be implemented and realized as well as explain basics of adaptive linear prediction.

An Exemplary Improved Heart Rate Monitoring Apparatus and Method

FIG. 2 illustrate a system view of a heart rate monitoring apparatus, according to some embodiments of the disclosure. The system provides an arrangement of parts for implementing or enabling a method for tracking a slow varying frequency present in one or more input signals provided by one or more sensors in a noisy environment. Similar to FIG. 1, the apparatus includes a light source 102, an optical sensor 104. The light source can be a light emitting diode (LED), or any suitable component for emitting light. The light emitted by the light source 102 for measuring heart rate (e.g., blood volume) can be any suitable wavelength depending on the application. The apparatus can include a plurality of light sources emitting a range of wavelengths of light. The optical sensor 104 may be the same device as the light source 102, or the optical sensor 104 may be provided near the light source 102 to measure light near the optical sensor 104, e.g., to measure absorption of light emitted by the light source 102 in the skin to implement PPG. In addition, the apparatus includes an accelerometer 110 to measure acceleration/motion of the overall apparatus. Furthermore, the apparatus may, optionally, include other sensors 202 or other types of sensors, which can provide information to assist in filtering of the input signal and/or heart rate tracking. An integrated circuit 204 can be provided to drive the light source 102 and provide an analog front end 204 to receive signals provided by optical sensor 104, accelerometer 110, and other sensors 202. In some embodiments, the analog front end 204 can convert (if desired) analog input signals to data samples of the analog input signal. The analog front end can be communicate with a processor 206 to provide the data samples, which the processor 206 would process to track a slow varying frequency, e.g., the heartbeat.

In various embodiments, the processor 206 can include several special application specific parts or modules, electronic circuits, and/or programmable logic gates specially arranged for processing the data samples of the input signal to track the slow varying frequency. The processor 206 can be a digital signal processor provided with application specific components to track the slow varying frequency, and/or the processor can execute special instructions (stored on non-transitory computer readable-medium) for carrying out various methods of tracking the slow varying frequency as described herein. FIG. 3 illustrates an exemplary flow diagram of one such a method, e.g. implemented by the processor 206 shown in FIG. 2, for tracking a slow varying frequency present in one or more input signals provided by one or more sensors in a noisy environment, according to some embodiments of the disclosure. At a high level, the method includes a filter generation component 302, a signal conditioning component 304 (dependent on the filter generation component 302), and a tracking component 306 (dependent on the filter generation component 302 and/or the signal conditioning component 304). The method can continue back at the filter generation component 302 to process other data samples in the stream of data samples of the input signal.

Referring to both FIG. 2 and FIG. 3, in some embodiments, the parts of processor 206 can include one or more of the following: a filter coefficient generator 208, a signal conditioner 210, a tracker 212, and a reconstructor 216, e.g., to implement the method shown in FIG. 3.

The filter coefficient generator 208 implements functions related to the improved filtering mechanism (corresponding to filter generation component 302 of the method shown in FIG. 3) by using accelerometer data to generate a filter for filtering the input signal before providing the data samples to the tracker 212.

The signal conditioner 210 implement functions related to processing data samples of the input signal based on the decision(s) in the filter coefficient generator 208 to prepare the data samples for further processing by the tracker 212 (corresponding to signal conditioning component 304 of the method shown in FIG. 3). For instance, the signal conditioner 210 can filter data samples of the input signal a certain way (or apply a filter on the data samples), apply a mask to the data samples, attenuate certain data samples, modify the values of certain data samples, and/or select certain data samples from a particular sensor for further processing. The signal conditioning process can depend on the output(s) of the filter coefficient generator 208.

The tracker 212 implements functions related to tracking the slow varying frequency, e.g., the heartbeat, based on the output from the signal conditioner 210 (corresponding to tracking component 306 of the method shown in FIG. 3). In other words, the tracker continuously monitors the incoming data samples (raw data or as provided by the signal conditioner 210) and attempts to continuously determine the frequency of the slowly varying frequency present in the one or more signals from the sensors. The output of the tracker 212 represents an estimate of the heart rate in beats per minute, and can be provided to a user via output 214 (e.g., a speaker, a display, a haptic output device, etc.).

The reconstructor 216 can implement functions related to (re)constructing or synthesizing a time domain representation of the slow varying frequency, e.g., a heartbeat. Based on frequency information of the input signal, the reconstructor 216 can artificially generate a cleaner version of the input signal having the slow varying frequency (referred herein as the "reconstructed signal"). The reconstructed signal can be useful in many applications. For instance, the reconstructed signal can be provided to output 214 for display. The reconstructed signal can also be saved for later processing and/or viewing. Generally speaking, the reconstructed signal can be useful for users to visually and analytically assess the health of the living being with the irrelevant noise content removed. For instance, the reconstructed signal can assist healthcare professionals in assessing whether the living being has any underlying conditions relating to heart and arterial health. This reconstructed signal can be generated by first using the filter coefficient generator 208, the signal conditioner 210, and the tracker to track the slow varying frequency.

The filter coefficient generator 208, the signal conditioner 210, the tracker 212, and the reconstructor 216 can include means for performing their corresponding functions. Data and/or instructions for performing the functions can be stored and maintained in memory 218 (which can be a non-transitory computer-readable medium). In some embodiments, the filter coefficient generator 208 (corresponding to filter generation component 302 of the method shown in FIG. 3) can affect the processing performed in tracker 212 (corresponding to tracking component 306 of the method shown in FIG. 3). This feature is denoted by the arrow having the dotted line. The apparatus shown in FIG. 2 is merely an example of a heart rate apparatus, it is envisioned that other suitable arrangements can be provided to implement the improved method for filtering one or more input signals to track a slow varying frequency present in the input signals provided by heart rate sensors in a noisy environment.

Because the improved filtering mechanism of the input signal is based on using adaptive linear prediction, basics of this technique are now described.

Basics of Adaptive Linear Prediction Filters

A filter conditions an incoming signal and produces an output signal having certain selected or controlled characteristics. Coefficients of a filter determine its characteristics and output. Often, a specific output may be desired, but the coefficients of the filter cannot be determined at the onset. One example is an echo canceller where the desired output cancels the echo signal. In such a case, oftentimes the coefficients cannot be determined initially because they depend on changing transmission conditions. For such applications, one option may be to rely on adaptive filtering techniques.

An adaptive filter refers to a time-varying filter whose coefficients are adjusted in a way to optimize a cost function or to satisfy some predetermined optimization criterion. An adaptive filter may be considered to consist of two distinct parts: 1) a filter itself, where the structure of the filter is designed to perform a desired processing function, and 2) an adaptive algorithm configured to adjust the coefficients of the filter to improve its performance. The filter structure and the adaptive algorithm used in a particular adaptive filter depend on various design characteristics and acceptable trade-offs, such as e.g. a trade-off between accuracy and complexity of a filter.

An example of an adaptive filter is illustrated in FIG. 4, where an adaptive filter 402 includes a filter 402 and an adaptive algorithm 404. The incoming signal, $x(k)$, is applied to a shift register or other memory device, and the output $y(k)$ consists of a weighted sum of current and past samples of the input x. The adaptive algorithm adjusts the weights (i.e., the coefficients) in the filter to minimize the error, $e(k)$, between the filter output $y(k)$ and the desired response of the filter, $d(k)$, where $h(k)$ refers to impulse response of an adaptive filter. Such an adaptive filter can automatically adapt (i.e., self-optimize) in the face of changing environments and changing system requirements and can be trained to perform specific filtering and decision-making tasks according to some update equations that define the training rules. Therefore, adaptive filters have been widely used to enable signal processing techniques in a variety of applications requiring separation of signals of interest from noise.

In the case of adaptive linear prediction, there is only a single input (i.e., there is no desired response $d(k)$ of the filter), and the goal of the filter is to minimize the error between the input and a weighted sum of past values of the input. Signals that may be present at the input may be considered as belonging to one of the following classes. One class may be considered to include noise signals (which may be filtered and have a non-flat spectrum), while another class may be considered to include signals that consist of sums of sinusoids. For the input signals of the first class, an adaptive linear predictor acts as a whitening filter, and the output at the "prediction error" node will look like white noise. For the input signals of the second class, the signal is fully predictable, and if the prediction filter is long enough, the prediction error output will go to zero.

Figure 5:
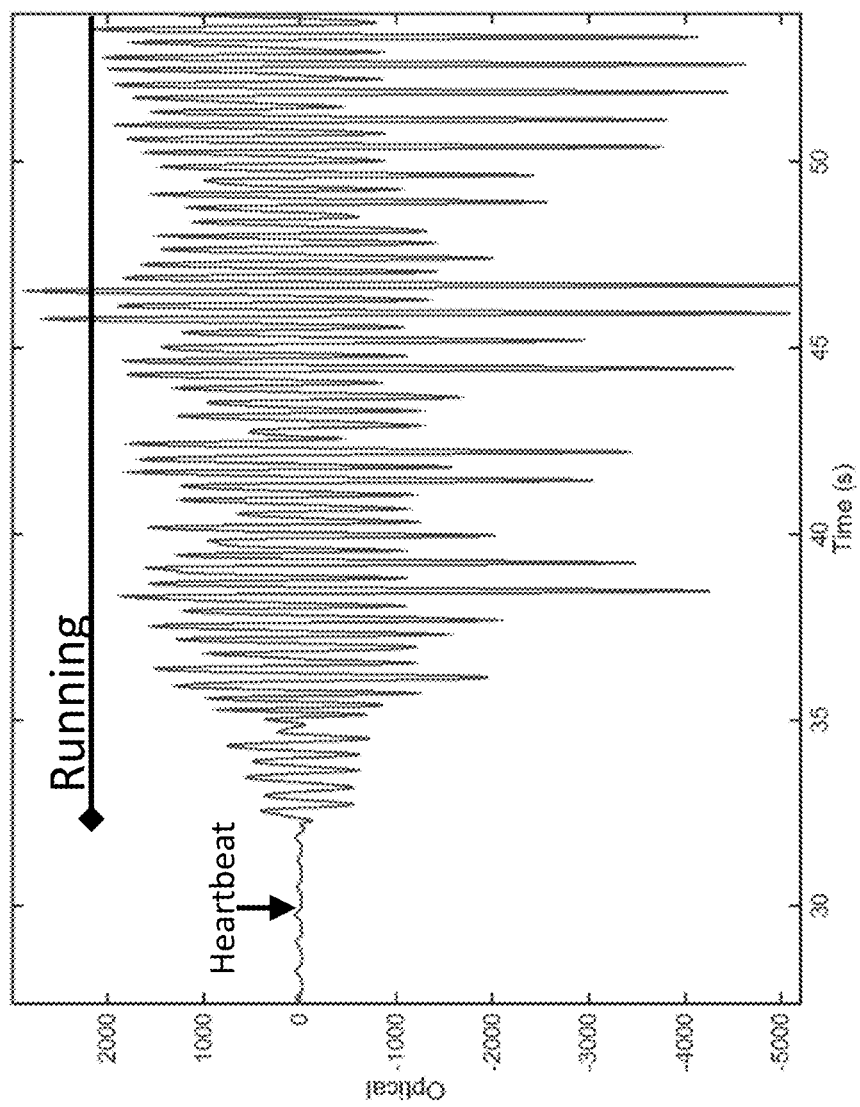
FIG. 5 illustrates an exemplary PPG signal as measured by an optical sensor, according to some embodiments of the disclosure.

Front-End Processing: Exemplary Implementation of an Improved Filtering Mechanism FIG. 5 illustrates a PPG signal (y-axis) as measured by an optical sensor, such as the sensor 104 described above, as a function of time (x-axis). FIG. 5 provides a clear illustration of technical challenges associated with tracking the heart rate within a PPG input signal because the heartbeat contribution in the PPG signal is very small compared to the very large noise from any motion, even small motion, present during e.g. running.

Embodiments of an approach described in this section, referred to herein as a "time-domain interference removal approach" or simply as a "time-domain interference removal," are based on recognition that using an ALP filter on the accelerometer data allows for generating filter coefficients which may then be used to filter the PPG signal prior to tracking the frequency of a heartbeat signal in the PPG signal. In general, the time-domain interference removal described herein includes applying the ALP to generate one or more sets of dynamically-varying filter coefficients, and then removing motion-related artifacts from the PPG signal using a copy of the generated filter coefficients, used in an identical filter inserted into the PPG signal path. The latter step may be described as a PPG interference removal by a "slave filter" with copied coefficients. In various embodiments, the ALP approach may include filtering based on the application of ALP coefficients to data from at least one, but possibly more, axes of the accelerometer. A full interference removal system with all three axes is also described herein.

Figure 6:
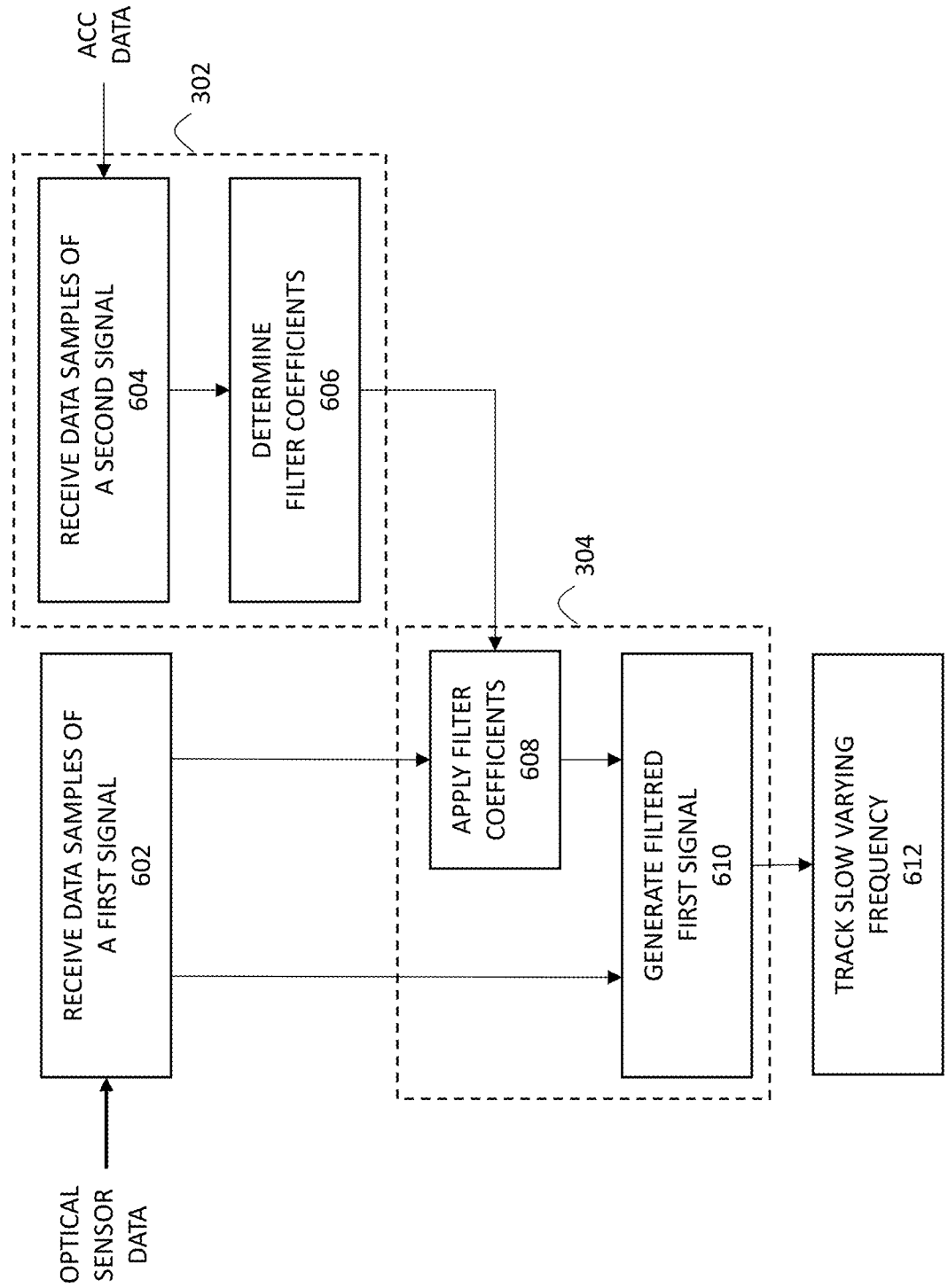
FIG. 6 illustrates an exemplary flow diagram of a method for filtering one or more input signals prior to tracking a heartbeat frequency present in the input signals, according to some embodiments of the disclosure.

FIG. 6 illustrates an exemplary flow diagram of a more detailed method 600 for tracking a heartbeat signal present in one or more input signals provided by one or more heart rate sensors in a noisy environment, according to some embodiments of the disclosure.

The method 600 includes receiving data samples of a first signal (i.e., an input signal) (step 602). The first signal can be generated by an optical sensor, and in some cases, the first signal is processed by an analog front end to produce (digital) data samples of the first signal.

The method 600 also includes receiving data samples of a second signal (step 604). The second signal can be generated by a device capable of detecting and quantifying motion of the heart rate sensors, such as e.g. an accelerometer. Preferably, the second signal is acquired at the same time as the first signal and the two signals are processed synchronously, thus providing the closest overlap between the motion of the heart rate sensors and the data acquired by the sensors. Similar to the first signal, in some cases, the second signal is processed by an analog front end to produce (digital) data samples of the second signal. The data samples of the second signal are received by the processor for adaptive filter operation.

Leveraging the insight that accelerometer measurements taken at the same time as the measurements by a heart rate sensor may be considered to accurately represent motion of the heart rate sensor when the input signal was acquired, the data samples of the second signal are then used to determine filter coefficients for a filter representative of motion detected by the accelerometer (step 606). To that end, adaptive linear prediction may be used, an exemplary implementation of which is illustrated in FIG. 7, where the variable X denotes values/signal provided from one of accelerometer axes, i.e. data samples of the second signal received in step 604 of FIG. 6.

Figure 7:
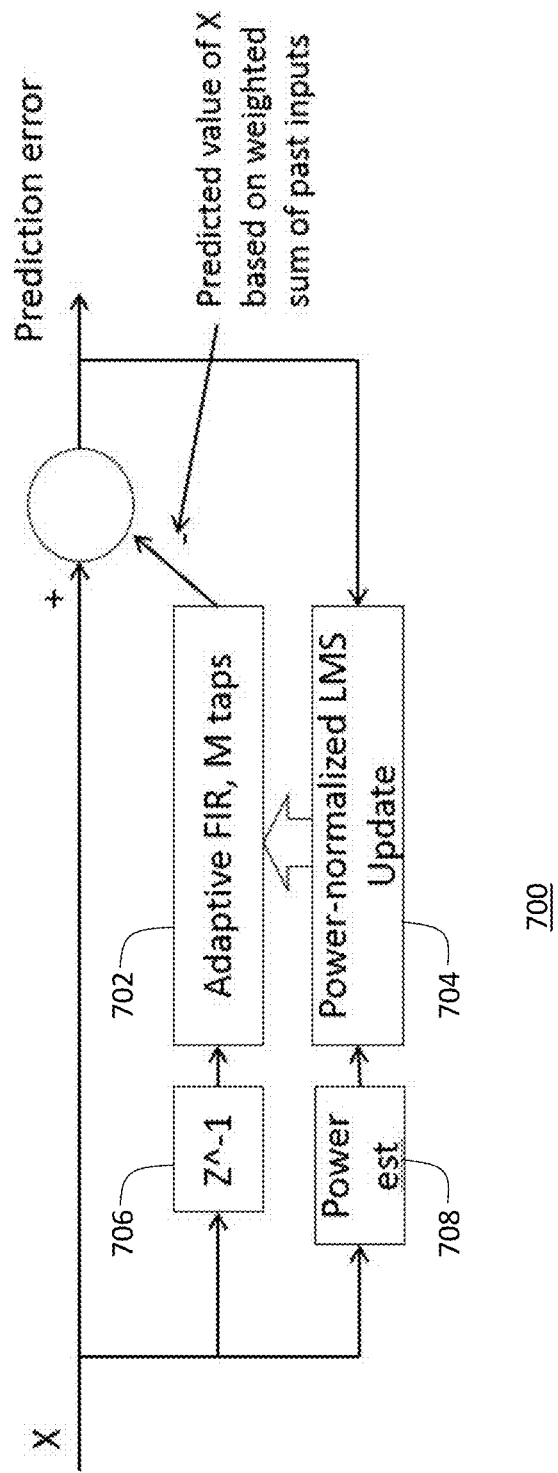
FIG. 7 illustrates power-normalized ALP, according to some embodiments of the disclosure.

As shown in FIG. 7, an ALP filter 700 includes a filter itself (analogous to the filter 402 shown in FIG. 4), shown as an adaptive filter 702, which could be, in one exemplary embodiment, a finite impulse response (FIR) filter with M taps. The ALP filter 700 further includes an adaptive algorithm (analogous to the algorithm 404 shown in FIG. 4), shown as a power-normalized least mean square (LMS) update algorithm 704. In addition, a power estimation element 708 may be provided, configured to estimate power of the second signal X, which power values are then provided to the power-normalized adaptive algorithm 704.

Further, the ALP filter 700 may include a single-sample delay $Z^{-1}$ 706, introduced before the filter 702, to ensure that the filter 702 only has access to past data samples of the second signal X. Variable "Z" is used in this illustration to denote that "Z" may stand for a Z-transform which is similar to the Laplace transform for continuous-time circuits except that in this case it is optimized for discrete-time processing used whenever the data is in a sampled form. Thus, in general, $Z^{-m}$ represents an m-sample delay. Variable m being equal to 1 indicates a single sample delay, but m could also be greater than one sample, which may be advantageous in some applications in view of the design tradeoffs as known in the art.

For the exemplary illustration of FIG. 7, the update equation for the kth finite impulse response (FIR) coefficient (denoted "c") at time n (i.e., for the nth data sample of input X) may be expressed as follows:

$$c(k,n)=c(k,n-1)+\text{alpha}*x(k,n)*\text{err}(n)/\text{power}(n),$$

where x(k,n) is the value stored in the k'th position of the FIR shift register at time n, c(k,n) is the k'th coefficient at time n, err(n) is the prediction error at time n, alpha is a constant that controls the convergence rate, and power is the average signal power averaged over the length of the FIR filter.

The ALP filter 700 may be used as an adaptive notch filter for filtering the optical signal detected by an optical sensor, such as the sensor 104 described above, from artifacts caused by the motion, which motion is detected by an accelerometer, e.g. the accelerometer 110 described above. The M-tap linear predictive filter 700 will try to adapt to reduce the error output to 0, which is possible if the signal is completely predictable based on a linear combination of the previous N samples. In the case where the second signal (i.e. accelerometer data from at least one axis) consists of sine waves+noise, the error output will consist of only noise, and can be viewed as a time-varying filter that will form notches in the frequency domain, aligned with the frequencies of the input sine tones. In the case where the second signal can be modeled as white noise filtered by an all-pole filter, the error output will consist of "whitened" noise, and the system can be viewed as a time-varying filter where the filter adapts to the inverse of the input spectrum (hence the term "adaptive spectral whitening" may be appropriate). Unlike other approaches for interference removal that rely on finding spectral peaks, such an approach is not limited to forming notch filters at certain frequencies. Instead, any signals that are "predictable" based on the previous M samples can be removed.

If there is no correlation between the error output and the data at given location in the FIR filter delay line, then the corresponding coefficient may wander/drift off to high values and create non-flat frequency responses in spectral regions where the source contains little energy. One solution to this could be to add a leak factor to the update equation, as follows:

$$c(k,n)=\text{leak}*c(k,n-1)+\text{alpha}*x(k,n)*\text{err}(n)/\text{power}(n)$$

In an embodiment, such a leak factor could be set to 0.99.

Returning back to the method 600 of FIG. 6, steps 604 and 606 may be considered to represent the filter coefficient generation 302 described in FIG. 3, as indicated with a dashed box labeled "302" around steps 604 and 606 in FIG. 6. On the other hand, steps 608 and 610 may be considered to represent the signal conditioning 304 described in FIG. 3, as indicated with a dashed box labeled "304" around steps 608 and 610 in FIG. 6.

As shown in FIG. 6, filter coefficients determined in step 606 are then applied to a filter which filters the data samples of the first signal, e.g. PPG signal (step 608). Applying the coefficients determined in step 606 identifies contributions in the first signal that are attributable to the motion of the heart rate sensor. Since such contributions are not related to the heartbeat, but, rather, are motion-related artifacts in the first signal, the result of step 608 is then subtracted from the first signal (step 610) to generate a filtered first signal where the amount of noise is reduced by eliminating or at least reducing noise due to the motion of the heart rate sensor. Steps 608 and 610 for the example of the ALP filter 700 shown in FIG. 7 are illustrated in FIG. 8.

Figure 8:
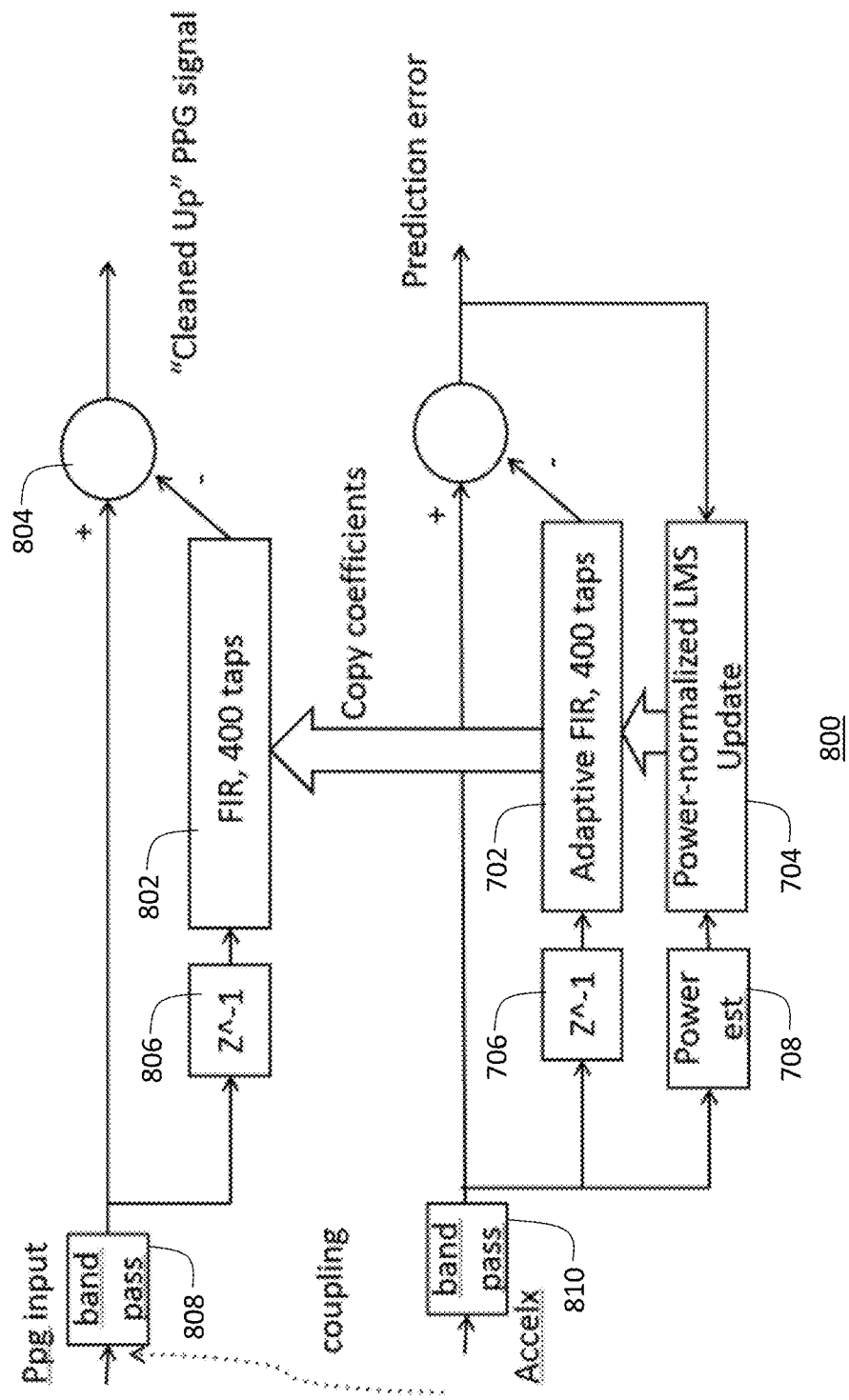
FIG. 8 illustrates time-domain interference removal for one accelerometer axis, according to some embodiments of the disclosure.

FIG. 8 illustrates time-domain interference removal 800 for one accelerometer axis, according to some embodiments of the disclosure. The coefficients from the ALP, generated as described with reference to FIG. 7, are applied to the PPG path, as shown in FIG. 8 with an arrow "Copy coefficients" between the adaptive FIR 702 of the ALP and the filter in the path of the PPG input (i.e., the first signal), which filter is shown as an FIR filter 802. In this manner, frequency-response notches may be applied to the PPG path, resulting in a PPG signal with less noise. Thus, the filter 802 shown in FIG. 8 represents applying the copied filter coefficients of step 608 illustrated in FIG. 6, while subtraction of the outcome of the filter 802 from the PPG input performed in element 804 shown in FIG. 8 represents generating the filtered PPG signal of step 610 illustrated in FIG. 6.

The example of FIG. 8 further illustrates a delay element 806, indicating that a one or more sample delay may be applied to the data samples of the first signal (similar to the delay applied to the data samples of the second signal with the delay element 706).

In addition, FIG. 8 illustrates that, prior to processing of the PPG input (first signal) and accelerometer data (second signal), in some embodiments, a filter may be applied to one or both of these signals to filter out contributions in each of these signals that cannot be attributable to the heartbeat. Such a filter is shown as a band-pass filter 808 for the first signal and a band-pass filter 810 for the second signal. Filters 808 and 810 are configured to filter out components outside of an expected range of frequencies representative of the slow varying frequency the method is tracking (i.e., a heartbeat). Typically, a heart rate is between 0.5 Hertz to 3.5 Hertz (in some cases it can be as high as 4 or 5 Hertz). If the first and second signals have prominent components outside of the reasonable frequency band of interest, it is likely the data samples do not have a trackable heartbeat.

The filtering using filters 808 and 810 could alternatively be performed at later points in time, but preferably before the step of tracking the heart rate. In an embodiment, filters 808 and/or 810 can be incorporated with a signal conditioning process by processing the data samples with a filter to substantially attenuate signal content outside of a reasonable frequency band of interest corresponding to the slow varying frequency of the input signal (or apply a masking process to achieve a similar effect) before extracting the heart rate information of the input signal. While the filters 808 and 810 are shown in FIG. 8 as band-pass filters (e.g., passing signals in the bandwidth from 0.5-3.5 Hertz, 0.5-4 Hertz, 0-4.5 Hertz, or similar variant thereof), in other embodiments one or both of these filters can be implemented as a low-pass filter (e.g., passing signals in a bandwidth from 0-3.5 Hertz, 0-4 Hertz, 0-4.5 Hertz or similar variant thereof). The type of filter used to attenuate signals outside of the reasonable frequency band of interest can vary depending on the application. Furthermore, the reasonable frequency band of interest can vary depending on the application. In one example, the reasonable frequency band of interest includes a frequency band of 0.5 Hertz to 3.5 Hertz (or includes frequencies between 0.5 Hertz to 3.5 Hertz), which is suitable for keeping frequency content that is more likely to be associated with a heartbeat.

Figure 9:
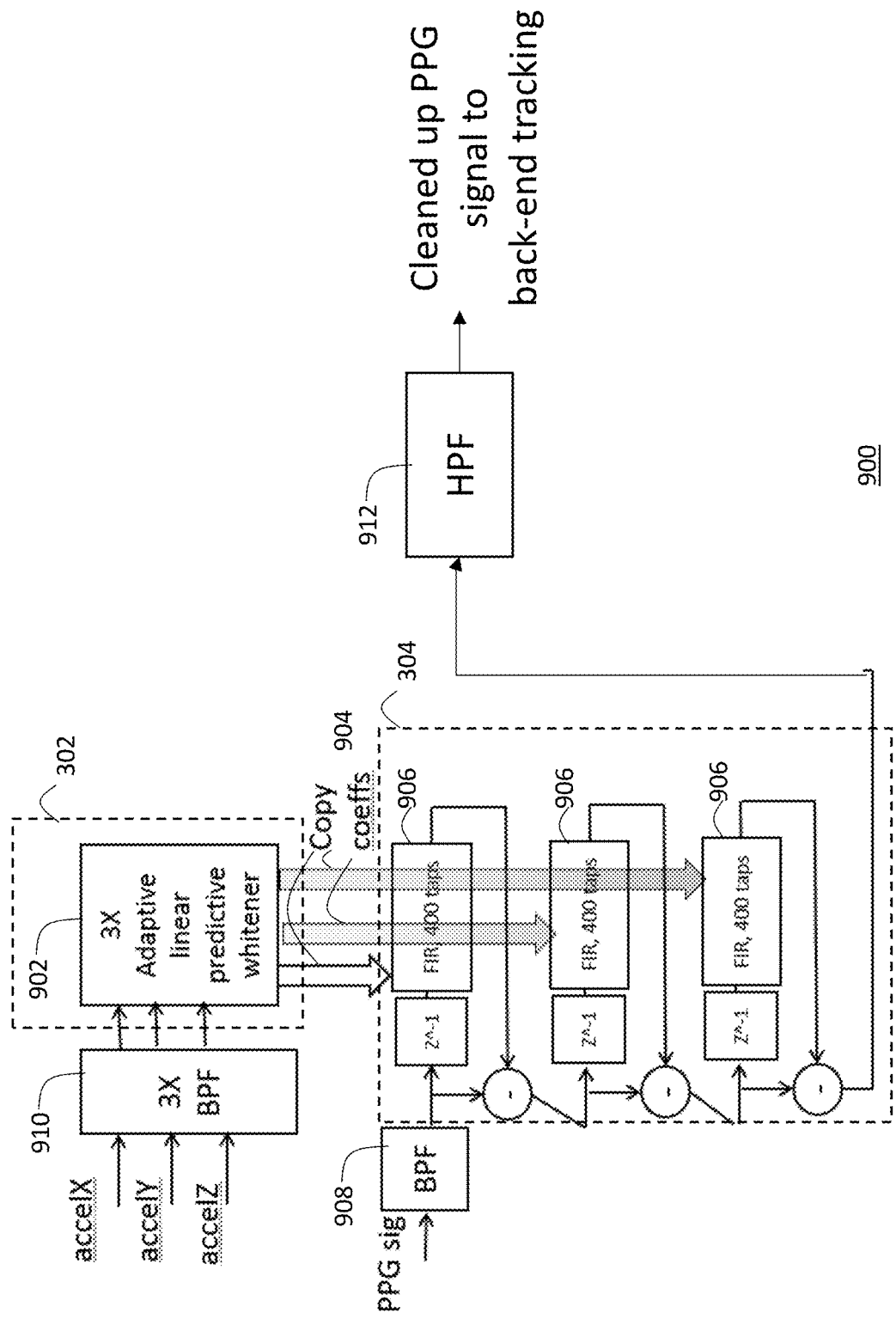
FIG. 9 illustrates complete front-end processing associated with time-domain interference removal for three accelerometer axes, according to some embodiments of the disclosure.

While FIG. 8 illustrates processing associated with time-domain interference removal for one accelerometer axis, FIG. 9 illustrates complete front-end processing 900 associated with time-domain interference removal for three accelerometer axes, according to some embodiments of the disclosure. Such an approach allows eliminating or reducing contributions in the PPG signal due to motion in each of the three orthogonal direction components, advantageously resulting in an improved filtered PPG signal which can then be used for tracking of the heartbeat frequency. Processing for each accelerometer axis for the implementation of FIG. 9 is analogous to that described in association with FIG. 8 and, therefore, in the interests of brevity, is not repeated here. In FIG. 9, a box 902 is intended to illustrate three ALP filters such as the ALP filter 700 shown in FIGS. 7 and 8, with one respective ALP filter per each one of the accelerometer axes. Since each one of the ALP filters 902 receives accelerometer data for the particular direction of motion, the coefficients derived by those filters and applied to the first signal can be, and are likely to be, different, as illustrated in FIG. 9 with individual arrows 904 "Copy coefficients" going to each one of the filters 906 in the PPG path. Thus, filters 906 are analogous to the filter 802 illustrated in FIG. 8.

As used herein, "BPF" illustrated in FIG. 9 in boxes 908 and 910 refers to "band-pass filter", such as e.g. the filters 808 and 810, respectively, described in association with FIG. 8 (i.e., at least some, or all, of the BPF filters illustrated in FIG. 9 could be low-pass filters). Although labeled with the same numeral, in some embodiments of the implementation of FIG. 9, the BPF filters 910 used in the different paths of the accelerometer axes, could be different for each accelerometer axis (similar to the ALP filters 902 also labeled with the same numeral in FIG. 9).

Furthermore, while FIG. 9 illustrates cascading of the filters 906 for filtering the incoming PPG signal, in other embodiments, such filters derived from multiple channels of an accelerometer may be combined differently (i.e., not necessarily by cascading at all or using cascading different from that shown in FIG. 9).

In FIG. 9, ALP whitener 902 may be considered to represent the filter generation 302 described in FIG. 3, as indicated with a dashed box labeled "302" around box 902 in FIG. 9. Similarly, filtering with the filters 906 may be considered to represent the signal conditioning 304 described in FIG. 3, as indicated with a dashed box labeled "304" in FIG. 9. In some embodiments, the BPF 908 may also be considered a part of the signal conditioning 304. Further, application of an optional high-pass filter ("HPF") 912 shown in the example of FIG. 9 may also be considered to be a part of the signal conditioning 304. Such a HPF may be used to reduce or eliminate possible high-frequency artifacts generated as a result of application of filters using coefficients derived from the ALP.

As shown in FIG. 9, the cleaned up PPG signal from the front-end is then provided to back-end frequency estimation module that tracks the heartbeat frequency and provides the heart rate. Returning back to the method 600 shown in FIG. 6, this means that, once the signal conditioning 304 has been performed on the first signal, the method 600 proceeds to tracking the heart rate (step 612).

One important advantage of the improved filtering mechanism described herein is its ability to filter the input signal from a heart rate sensor within the time-domain, thus eliminating the need to perform computationally intensive conversion to the frequency domain as used in frequency-domain approaches. Another important advantage is that it provides an improved manner for reducing or eliminating motion-related artifacts from the input signal. In particular, the filter generation using ALP allows proper signal conditioning to prepare input data samples that can lead to better tracking. This advantage can achieved by filtering, removing, attenuating, modifying, or removing certain undesirable portions of the data samples from the heart rate sensors prior to the data samples being processed to track the heart rate.

FIGS. 4-9 provide some examples of implementing the improved filtering method and some of the variations within these examples have been described above. The following section describes additional variations with respect to the time-domain interference removal described above.

Front-End Processing: Further Variations with Respect to the Improved Filtering Mechanism Steps 608 and 610 illustrated in FIG. 6 to represent the signal conditioning 304 provide one example of using the coefficients derived from the accelerometer data to condition the first signal. More generally, the signal conditioning 304 can include any method for performing signal conditioning of the data samples of the input signal to, e.g., filter, remove, or mask, portions of the data samples of the first signal which are likely associated with motion-related artifacts based on the filter generated using accelerometer data (i.e. data samples of the first signal which are likely not associated with a heartbeat).

While FIGS. 8 and 9 illustrate FIRs comprising 400 taps, of course other implementations could include any other number of taps or even different kinds of filters, such as adaptive lattice filters or adaptive Infinite Input Response (IIR) filters. The number of taps selected for a particular implementation affects the number of notches that may be formed in the frequency domain and the possible locations of those notches in frequency.

Furthermore, while filters described above are sometimes described as notch filters (i.e., a band-stop filter with a narrow stopband (high Q factor) having a flat response everywhere besides the band that is passes), in general filters generated by the ALP could comprise any kind of more nuanced filters with non-zero response outside of the passband.

While FIGS. 7-9 illustrate the filter structures to be implemented as Finite Input Response (FIR) filters, embodiments of the present disclosure are applicable to other filter structures. Similarly, while FIGS. 7 and 8 illustrate the adaptive algorithms to be implemented as power-normalized LMS updates, LMS merely provides one exemplary way of updating a filter and other adaptive algorithms with minor modifications that would be apparent to a skilled person based on the discussions provided herein may be used. In particular, adaptive algorithms that may be higher performing than LMS may be implemented (even though such algorithms may be more complex).

While many examples described herein are described in relation to a frequency representative of a heartbeat, it is envisioned that the method can be applicable in other scenarios for filtering an input signal used for tracking other types of slowly varying frequencies (e.g., phenomena or events which has a frequency that does not change or jump abruptly). Furthermore, while the examples herein are described with one or more input signals provided by one or more optical sensors, it is envisioned that the method can be used to filter the input signals generated by other types of sensors, including but not limited to: optical sensor, audio sensor, capacitive sensor, magnetic sensor, chemical sensor, humidity sensor, moisture sensor, pressure sensor, and biosensor.

Furthermore, more than one optical sensor may be used and data obtained therefrom may be filtered according to the improved filtering method described above. Some considerations for using more than one optical sensors are described in the following section.

Using More than One Optical Sensor

The wavelengths used for measuring input signals for PPG can span wavelengths from blue to infrared. In classic applications, LEDs of two colors—often 660 nm and 940 nm—are used for measuring blood oxygen saturation. These devices are in large volume production and are readily available. In yet another application, a simple single-color LED—say at 940 nm, may be used to measure heart rate by measuring the periodic variation in a return signal. In some cases, a green LED is used to pick up variation in absorption caused by blood flow on the wrist.

Different wavelengths of light reflects differently from skin (due to the pigmentation and wrinkles, and other features of the skin) and different optical sensors tend to behave differently in the presence of motion when sensing light reflected from skin. Based on this insight, it is possible to infer information about presence of motion and/or the quality of an input signal. It is also possible to improve the data samples to be processed by the tracker based on the insight. Multiple light sources having different wavelengths can be used (e.g., a red LED and a green LED). For instance, by sensing these light sources and examining differences between the input signals of optical sensors for detecting light having respective wavelengths, or different portions of a spectrum of an input signal from a wideband optical sensor, it is possible to infer whether certain data samples of the input signal is likely to have been affected by motion or some other artifact.

Broadly speaking, an internally consistent model can be provided if different characteristics and behavior of different types of optical sensors under various conditions (or in general) are known. Based on the internally consistent model, information about the signal or the environment of the sensors can be inferred. The inference can assist the adaptive filter coefficient generators in assessing whether certain portions of the data samples should be removed. The inference can also assist signal conditioning to specify how the data samples should be processed to improve tracking. This can include filtering the signal a certain way. The inference can also, in some cases, signal to the tracker to perform tracking differently.

In some instances, the use of multiple optical sensors can improve tracking by removing or subtracting common global characteristics between optical sensors to better track the slow varying frequency. In some cases, the internally consistent model may prescribe that the tracked slowly varying frequency (e.g., the tracked heart rate) should be substantially the same for a plurality of sensors (e.g., the red LED should measure the same heart rate as the green LED).

Back-End Processing: Overview of an Improved Tracking Mechanism

Even after the signal conditioning to clean up the acquired input signal, e.g. using the improved filtering technique described above or any other appropriate signal conditioning technique, the input signal is oftentimes still very noisy so care should be taken in extracting the actual heart rate. The present disclosure describes an improved back-end processing mechanism that allows tracking of a heartbeat signal even in presence of noise in the input signal.

The improved tracking mechanism is based on recognition that feeding the input signal to a two-filter structure, where both filters pass a narrow band of frequencies around a resonant frequency F_RES and have substantially equal amplitudes at frequency F_RES, and further have the characteristic that above the resonant frequency F_RES, the amplitude of the first filter becomes larger than the amplitude of the second filter, and, below the resonant frequency F_RES, the amplitude of the second filter becomes larger than the amplitude of the first filter, then the frequency of the input signal can be identified by adaptively modifying the resonant frequency of both filters until the amplitudes of the outputs of the two filters are equal. As a result, identification/tracking of the heartbeat signal from a noisy sensor signal is possible.

One particularly useful two-filter structure that fits the description above may be provided as a Chamberlin state-variable filter. The following passages describe in further detail how the improved tracking mechanism can be implemented and realized as well as explain basics of state-variable filtering.

Back-End Processing: Exemplary Implementation of an Improved Tracking Mechanism

Figure 10:
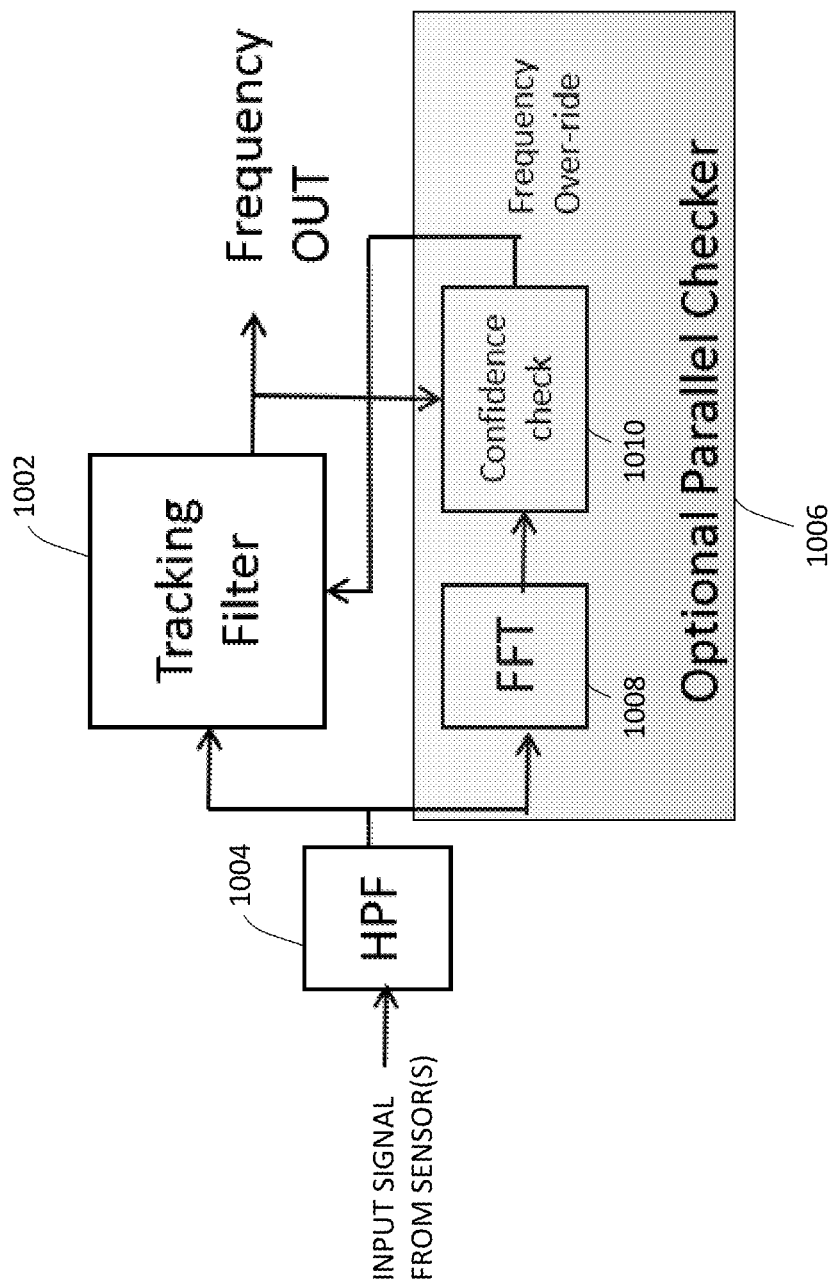
FIG. 10 illustrates exemplary back-end processing, according to some embodiments of the disclosure.

FIG. 10 illustrates exemplary back-end processing, according to some embodiments of the disclosure. While the front-end processing described above may be considered to be a first stage of heart rate monitoring, the back-end processing may be considered to be a second stage which comprises the actual tracking of the heart rate in the input signal, e.g. a PPG signal described above.

As shown in FIG. 10, an input signal from the heart rate sensor is provided to a tracking filter 1002. Such a signal could be e.g. a raw input signal as generated by the heart rate sensors or an input signal that has undergone some minimum processing, e.g. filtering to only keep frequencies in the range of interest (e.g. 0.5-3.5 Hz). Such a signal could be e.g. as one received in step 602 shown in FIG. 6. Alternatively, such a signal could be an input signal processed to reduce the amount of noise in it, e.g. such as a cleaned up input signal generated in step 610 shown in FIG. 7. In such a case, optionally, a HPF 1004 may be used to remove low-frequency artifacts that could be introduced by the ALP filtering (i.e., the HPF 1004 is analogous to the HPF 912 shown in FIG. 9). The input signal could also be a signal processed by any other signal conditioning technique as known in the art (in which case the HPF 1004 is likely not necessary).

In an embodiment, an optional parallel checker 1006 may be implemented, as also shown in FIG. 10. Such an optional checker may be configured to perform checks to make sure that the tracking filter is following the true heartbeat signal.

One algorithm performed by the checker 1006 may be described as follows. A Fast Fourier Transform (FFT) component 1008 may be employed, operating e.g. once per second, and operating on a buffer containing the most recent data samples, e.g., the buffer may contain data from the previous 5 to 10 seconds. The input signal is provided to such an FFT component, as shown in FIG. 10. As a result of performing FFT, a matrix of time-frequency bins is filled out with values and a confidence check component 1010 is examines the values to determine the confidence of the frequency outcome reported by the tracking filter 1002. Various criteria could be employed by the confidence checker 1010. In an embodiment, to produce a "confident" result, the frequency of the peak bin could not vary by more than +/−20% over 10 consecutive FFT frames, where a new frame is computed every second and has a length of 512 or 1024 with a typical sample-rate of 100 Hz and using any common window function and/or the amplitude of the peak bin could be larger than 1.6 times the next-lowest peak for 10 consecutive frames. If a "confident" result is obtained, the confidence checker 1010 may be configured to reset the tracking filter 1002 to the frequency corresponding to the peak bin. Thus, if two numbers agree (within a certain percentage), then the tracking filter is tracking properly, and otherwise the tracking filter 1002 may be reset.

In other embodiments, the checker 1006 may implement other algorithms that could monitor the broader spectrum of frequencies and make sure that the tracking filter 1002 is tracking the frequency corresponding to the heartbeat.

Figure 11:
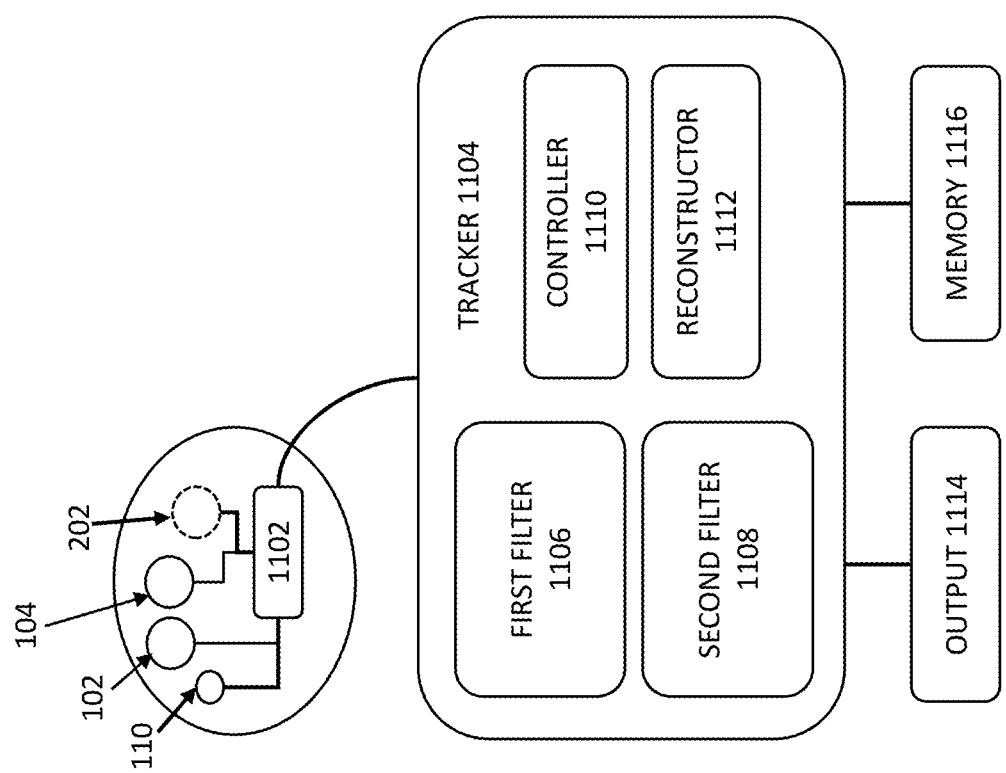
FIG. 11 illustrate a system view of a heart rate monitoring apparatus, according to some embodiments of the disclosure.

One exemplary implementation of a tracking filter 1002 is illustrated in FIG. 11 and is now described.

FIG. 11 illustrate a system view of a heart rate monitoring apparatus 1100, according to some embodiments of the disclosure. Similar to FIG. 2, the apparatus 1100 includes a light source 102 and an optical sensor 104. Optionally, the apparatus 1100 may include other sensors 202 and an optional accelerometer 110, as described above with reference to FIG. 2. An integrated circuit 1102 can be provided to drive the light source 102 and provide an analog front end to receive signals provided by the optical sensor 104 as well as, optionally, by the accelerometer 110 and other sensors 202. In some embodiments, the analog front end 1102 can convert (if desired) analog input signals to data samples of the analog input signal. The analog front end can communicate with a tracker 1104 to track a frequency of a heartbeat signal from the input signal acquired by the sensor 104. The tracker 1104 is analogous to the processor 206 with the tracker 212, described above (in which case the filter coefficient generator 208 and the signal conditioner 210 may be present, but are entirely optional).

Figure 12:
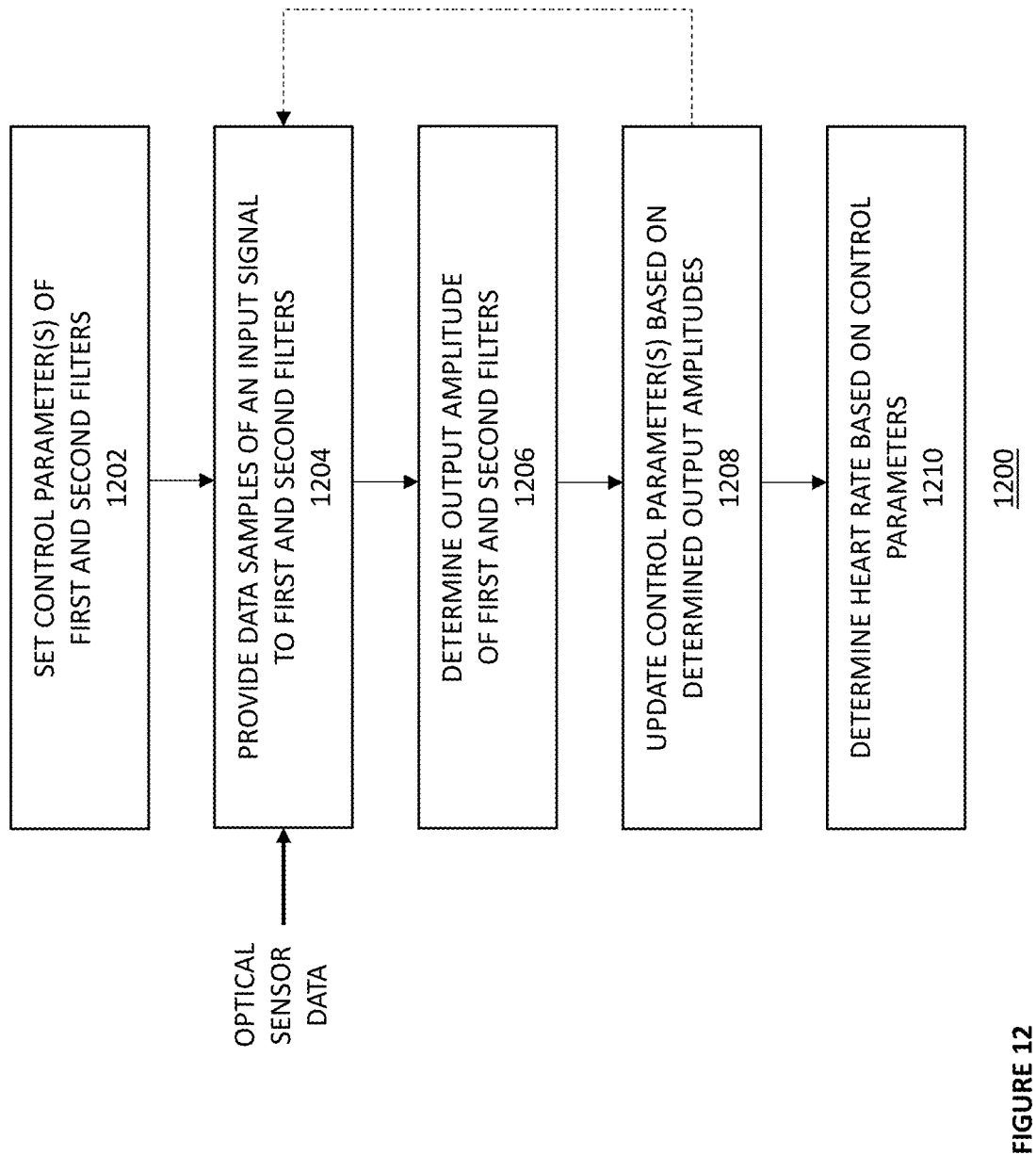
FIG. 12 illustrates an exemplary flow diagram of a more detailed method for tracking a heartbeat signal present in one or more input signals provided by one or more heart rate sensors in a noisy environment, according to some embodiments of the disclosure.

In various embodiments, the tracker 1104 can include several special application specific parts or modules, electronic circuits, and/or programmable logic gates specially arranged for processing the data samples of the input signal to track the frequency of the heartbeat signal from the input signal. The processor 1104 can be a digital signal processor provided with application specific components to track the slow varying frequency, and/or the processor can execute special instructions (stored on non-transitory computer readable-medium) for carrying out various methods of tracking the slow varying frequency as described herein. FIG. 12 illustrates an exemplary flow diagram of one such a method, e.g. implemented by the tracker 1104 shown in FIG. 11, for tracking the heart rate.

Referring to FIG. 11, in some embodiments, parts of the tracker 1104 may include one or more of the following: a first filter 1106 ($FILTER_A$), a second filter 1108 ($FILTER_B$), a controller 1110, and a reconstructor 1112.

The first filter and the second filter are filters that have a resonant frequency F_RES at which the amplitude of their outputs are substantially equal (such amplitude being of a non-zero value and typically at a or close to a resonant peak) and for which, above the frequency F_RES, the amplitude of the first filter becomes larger than the amplitude of the second filter, and, below the frequency F_RES, the amplitude of the second filter becomes larger than the amplitude of the first filter (i.e., the first and second filters have asymmetric response). In some embodiments, such first and second filters may be implemented as parts of a single state-variable filter, such as e.g. a Chamberlin filter. In various embodiments, such first and second filters may be implemented within a single filter (e.g. Chamberlin filter or other state-variable filters) or as separate filters, as long as the first and second filters are provided with a feedback loop that allows updating one or more control parameters of the filters that control the resonant frequency of the filters until the amplitudes of their outputs are equal.

The controller 1110 implements functions related to the improved tracking mechanism, as described in greater detail below. In some embodiments, the controller 1110 continuously monitors the incoming data samples of one or more signals from the heart rate sensor (an input signal) and attempts to continuously determine the frequency of the heartbeat signal present in the one or more signals from the sensors. The output of the controller 1110, e.g., determined heart rate in beats per minute, can be provided to a user via output 1114 (e.g., a speaker, a display, a haptic output device, etc.).

The reconstructor 1112 is analogous to the reconstructor 216 and, therefore, in the interests of brevity, the description is not repeated here.

The first filter 1106, the second filter 1108, the controller 1110, and the reconstructor 1112 can include means for performing their corresponding functions. Data and/or instructions for performing the functions can be stored and maintained in memory 1116 (which can be a non-transitory computer-readable medium).

The apparatus shown in FIG. 11 is merely an example of a heart rate apparatus, it is envisioned that other suitable arrangements can be provided to implement the improved method for tracking a hear rate from one or more input signals provided by heart rate sensors in a noisy environment.

FIG. 12 illustrates an exemplary flow diagram of a more detailed method 1100 for tracking a heartbeat signal present in one or more input signals provided by one or more heart rate sensors in a noisy environment, according to some embodiments of the disclosure. The method 1200 may be performed by the controller 1110 and/or by the tracker 212. The method 1200 may begin with setting initial control parameters for the first and second filters (step 1202). In some embodiments, such control parameters could include one or more parameters, e.g. coefficients, of digital FIR or digital IIR filters, or one or more parameters of a state-variable filter. The control parameters for the first and second filters can be, but do not have to be the same. Initial setting of the control parameters may be optimized to e.g. match the typical heart-rate of a person at rest. The control parameters of the filters control the resonant frequency F_RES. Therefore, setting/updating (i.e. changing) control parameters means setting/updating the resonant frequency F_RES of the first and second filters.

The method 1200 also includes receiving data samples of an input signal and providing the received data samples to the first filter 1106 and the second filter 1108 (step 1204). The input signal can be generated by an optical sensor, and in some cases, the input signal is processed by an analog front end to produce (digital) data samples, possibly subject to signal conditioning, of the input signal.

In response to receiving the input signal, the first and second filters produce an output. In step 1206, the method includes determining an amplitude of an output of the first filter (amplitude A) and an amplitude of an output of the second filter (amplitude B). An amplitude may be expressed e.g. in terms of a mean square value, root mean square value, peak-to-peak value, or any other measures that represent amplitude of an output signal.

Based on the determined amplitudes A and B, in step 1208, the method includes updating one or more control parameters. In particular, when the amplitude A is not equal to amplitude B, updating the control parameters aims to equalize these amplitudes by shifting the resonant frequency F_RES to be equal to the input frequency. In other words, control parameters are updated so that the amplitudes A and B would become equal. The resonant frequency F_RES of first and second filter moves up or down in frequency according to a change in the updated values of the control parameters.

Some filter topologies such as a state-variable filter, described in greater detail below, have a very simple mathematical relationship between the resonant frequency F_RES and the filter control parameters that control the frequency F_RES, and these topologies may be preferred in implementation for the sake of reducing the computational burden.

Figure 13:
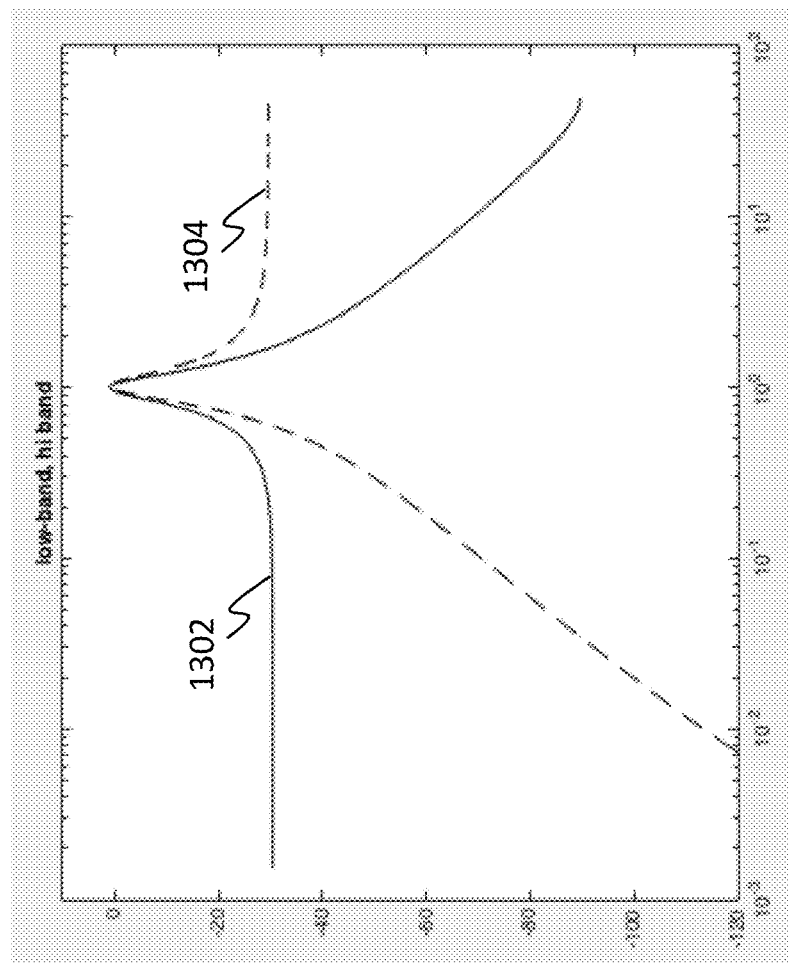
FIG. 13 illustrates outcomes of a low-pass filter and a high-pass filter, according to some embodiments of the disclosure.
Figure 14:
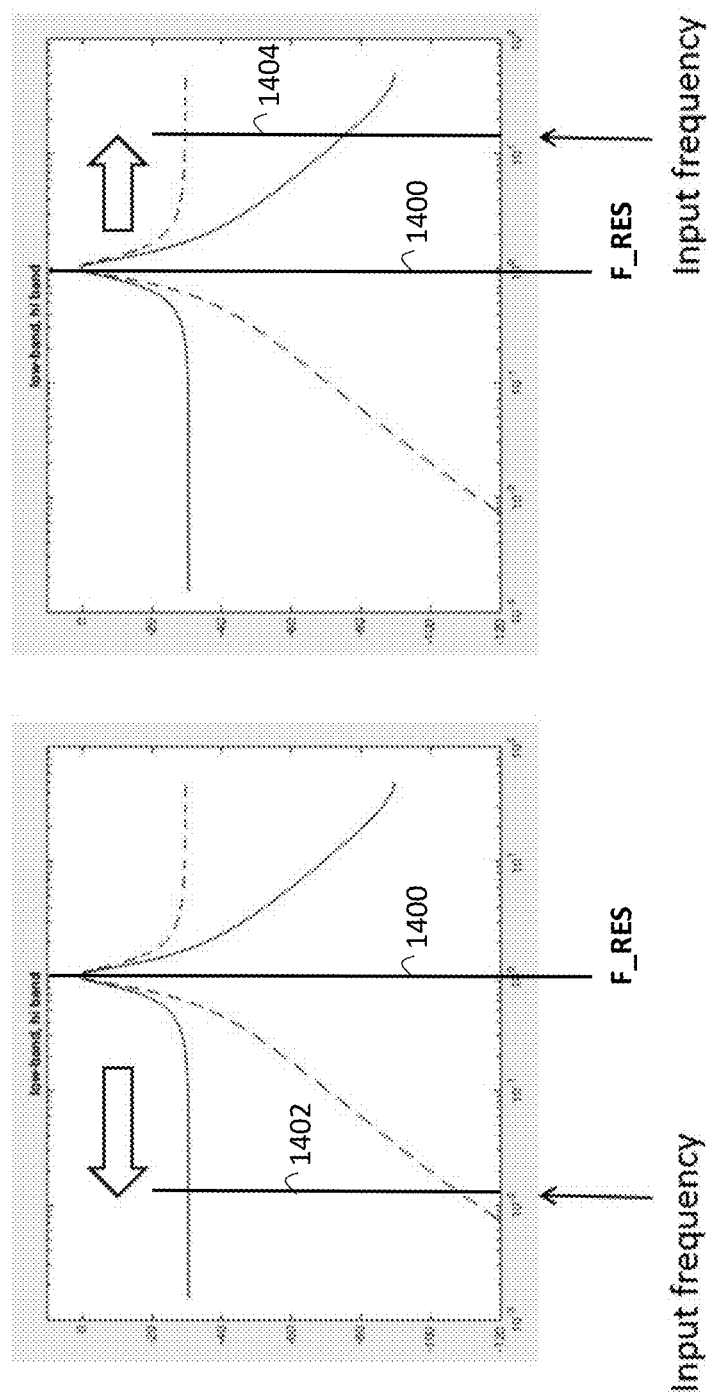
FIG. 14 illustrates steering of a filter output, according to some embodiments of the disclosure.

Steering of a filter output by means of updating control parameters is illustrated in FIGS. 13 and 14 described below.

In an optional embodiment, control parameters may also be updated based on a signal indicative of motion of the heart rate sensor during the acquisition of the input signal from which the heartbeat signal is being tracked. Such a signal may e.g. comprise an accelerometer signal as described herein. In one further embodiment, depending on how much motion is experienced during the acquisition of the income signal, the Q factor of at least one but preferably both of the first and second filters may be dynamically adjusted, e.g. by dynamically altering a Q factor of one or more $2^{nd}$-order IIR filters. Considerations for adjusting the Q-factor are described below with reference to FIG. 20.

The method 1200 also includes determining the frequency of the heartbeat signal based on the current values of the control parameters (i.e. based on the current value of F-RES) (step 1210). In general, a suitably-scaled and processed version of one or more control parameters can be used as the output heart-rate. In the case where the heart-rate is rapidly changing, the control loop may not track quickly enough to give an accurate representation of the instantaneous heart-rate, but in general it is acceptable to have some lag between the true heart-rate and the heart-rate presented to the user, as long as the lag is not excessively long. Therefore it may be acceptable to directly output a scaled version of one or more control parameters as the output heart-rate. However, there may be several conditions where the signal quality is very poor, or where the analog-to-digital converter (ADC) may be saturated, or any other condition that might indicate low confidence in the heart-rate estimate, where it might be desirable to freeze the heart-rate display or indicate an error. In this case, the calculated or presented heart-rate may differ from simple scaled version of the control parameters.

In some cases there may be a non-linear relationship between the values of the one or more control parameters and the true resonant frequency of the first and second filters. Thus if the values of the one or more control parameters are simply scaled and used as the output heart-rate, some error may be present. This error can be eliminated by including some deliberate non-linearity designed to compensate for the non-linear relationship between the one or more control parameters and the resonant frequency of the first and second filters.

If the amplitudes are not yet equal, the method may proceed from step 1208 to step 1204, i.e. steps 1204-1208 are iterated until the amplitudes of the outcomes of the first and second filters are substantially equal.

Steering of a filter output by means of updating control parameters is illustrated in FIGS. 13 and 14 for an example of the first filter being implemented as an under-damped high-pass filter and the second filter being implemented as an under-damped low-pass filter.

FIG. 13 illustrates outcomes of a low-pass filter (solid line 1302) and a high-pass filter (dashed line 1304), according to some embodiments of the disclosure. These two filters may be steered by comparing the outputs, as shown in FIG. 14.

FIG. 14 illustrates steering of a filter output, according to some embodiments of the disclosure. The plots on both sides of FIG. 14 illustrate, with a line 1400, frequency F_RES at which amplitudes of the outputs of the first and second filters are equal (in both plots line 1400 goes through the peaks where the amplitudes are equal).

The plot on the left side of FIG. 14 illustrates a case where the PPG input frequency is below the resonant frequency F_RES of the two filters. In this case the amplitude of the output of the high-pass filter is smaller than the amplitude of the output of the low-pass filter. Thus, the amplitude (e.g. mean square value) of the high-pass filter divided by the amplitude (e.g. mean square value) of the low-pass filter is less than 1 (or, phrased in an alternative manner, the difference of these amplitudes is negative). In such a case, the one or more control parameters need to be updated to shift the resonant frequency F_RES (at which responses of the first and second filters are equal) down, as shown with an arrow in the plot.

The plot on the right side of FIG. 14 illustrates a case where the PPG input frequency is above the resonant frequency F_RES of the two filters. In this case the amplitude of the output of the high-pass filter is larger than the amplitude of the output of the low-pass filter. Thus, the amplitude (e.g. mean square value) of the high-pass filter divided by the amplitude (e.g. mean square value) of the low-pass is greater than 1 (or, phrased in an alternative manner, the difference of these amplitudes is positive). In such a case, the one or more control parameters need to be updated to shift the resonant frequency F_RES up, as shown with an arrow in that plot.

In an embodiment, the first and second filters may be implemented as a Chamberlin state-variable filter, a brief review of which is provided in the following section.

Basics of State-Variable Filters

An analog state-variable filter refers to a type of active filter (i.e. a filter using active components such as e.g. an amplifier), that includes one or more integrators (i.e. components whose output is a time integral of its input signal) connected in some feedback loop configuration. A state variable filter directly realizes a state-space model, where an instantaneous output voltage of one of the integrators corresponds to one of the state-space model's state variables.

The Chamberlin Filter is one type of digital filter that approximates an analog state-variable filter, and could be used to implement the first and second filters as described herein. The name "Chamberlin" is derived from the fact that such a state variable filter was first described in Hal Chamberlin's "Musical Applications of Microprocessors," by straight-forward replacement of components from an analog state variable filter with digital counterparts. The Chamberlin filter provides a convenient way of implementing the first and second filters as described herein due to the fact that low-pass, high-pass, band-pass, and band-reject outputs are available simultaneously, and also because cutoff (or resonant) frequency and Q control are independent and their values can be calculated easily.

Figure 15:
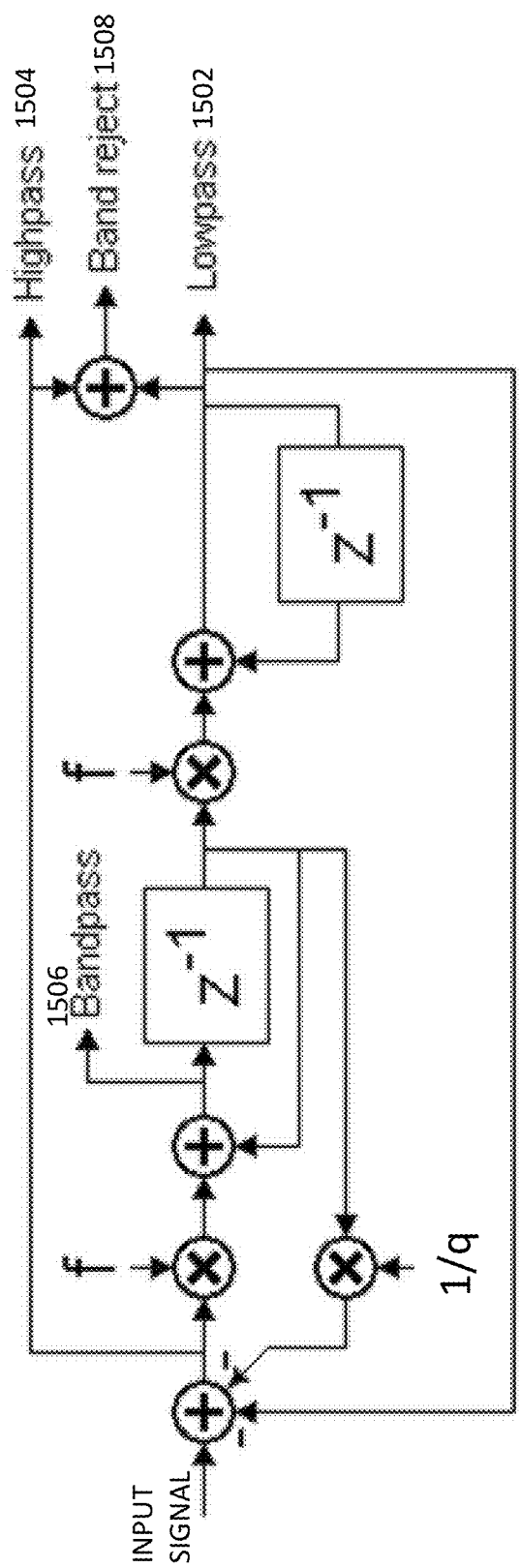
FIG. 15 illustrates a Chamberlin state-variable digital filter, according to some embodiments of the present disclosure.

FIG. 15 illustrates a Chamberlin state-variable digital filter, according to some embodiments of the present disclosure. Using such a filter (or another type of a state-variable filter) may be considered as the first step of using the tracker 1104/212. The parameter f can be computed from the corner frequency using:

$$f = 2\pi f_c / f_s$$

where $f_c$ refers to a corner frequency of the filter (a design parameter that is set depending on a particular implementation) and $f_s$ refers to the sampling rate (also a design parameter). In the case where highly-resonant filters are required, the frequency $f_c$ may also be called the resonant frequency, and is the same as the frequency F_RES shown in FIG. 14. The low-pass, high-pass, band-pass, and band-reject (i.e. notch filter) outputs are shown as outputs 1502, 1504, 1506, and 1508, respectively.

Figure 16:
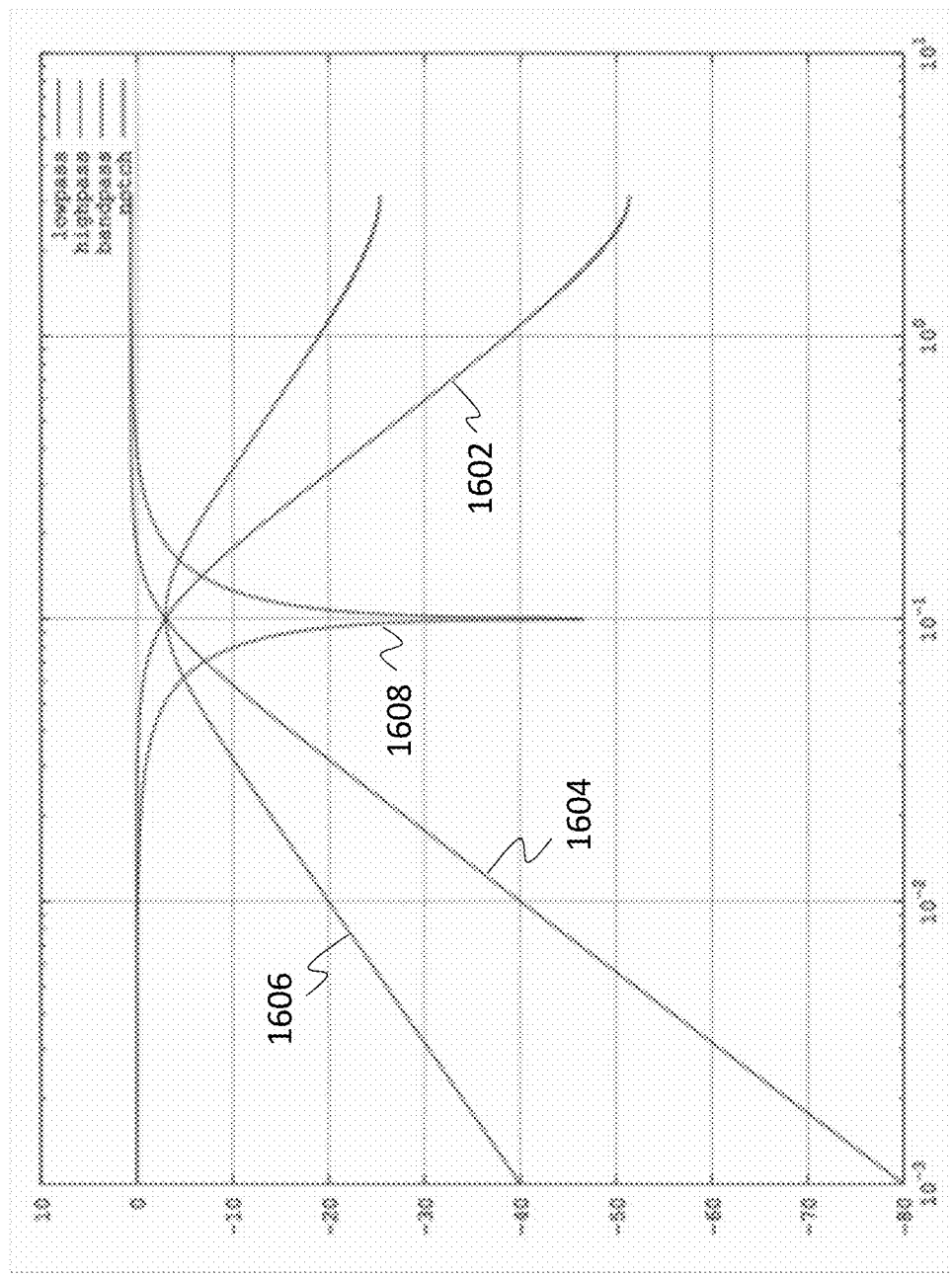
FIG. 16 illustrates responses from each output of a Chamberlin state-variable digital filter, according to some embodiments of the disclosure.

FIG. 16 illustrates responses from each output of a Chamberlin state-variable digital filter, according to some embodiments of the disclosure. The responses are shown as a response 1602 from a low-pass filter output of the filter of FIG. 15, a response 1604 from a high-pass filter output of the filter of FIG. 15, a response 1606 from a band-pass filter output of the filter of FIG. 15, and a response 1608 from a notch filter (band-reject) output of the filter of FIG. 15.

Turning back to FIG. 15, input "f" shown in the FIGURE represents an example of a control parameter described with reference to FIG. 12 (i.e., only one control parameter in this case). The Chamberlin filter is tuned by varying the value of this input parameter f, which tunes the value of F_RES. The goal of a tracking algorithm described herein is to find the value of the control parameter f at which the amplitudes of the two filters (in this example, the low-pass and the high-pass outputs of a Chamberlin filter) match. The latter (i.e., low-pass and high-pass outputs of a Chamberlin filter have the same amplitude) happens when F_RES is equal to the input frequency of the input signal to the Chamberlin filter.

One advantage of a Chamberlin filter is that the filter resonant frequency F_RES can be tuned with a single control parameter (input "f") and, therefore, frequency F_RES, where the outputs of the first and second filters are equal, can be determined by simply tuning this single parameter.

If the "Q" factor is set to a large value (more than 2, for example), the low-pass output and the high-pass output of a Chamberlin filter exhibit a resonant response (i.e. have a resonant peak) at the frequency F_RES, the value of which depends on the value of the control parameter "f", where the amplitudes of the low-pass and the high-pass outputs are the same. In general a large value of Q is advantageous in this context as it helps to reduce the sensitivity to noise and interfering signals which are not at the same frequency as the desired signal.

Using Cascaded Filters

Using one stage of a first and a second filter to tune the control parameters of the filters until their amplitudes are equal is sufficient to track heart rate frequency from the control parameters at which the amplitudes are equal. However, using a cascaded architecture may provide further advantages because it may allow for increased resolution in frequency (i.e. steeper drop off from the resonant frequency).

Figure 17:
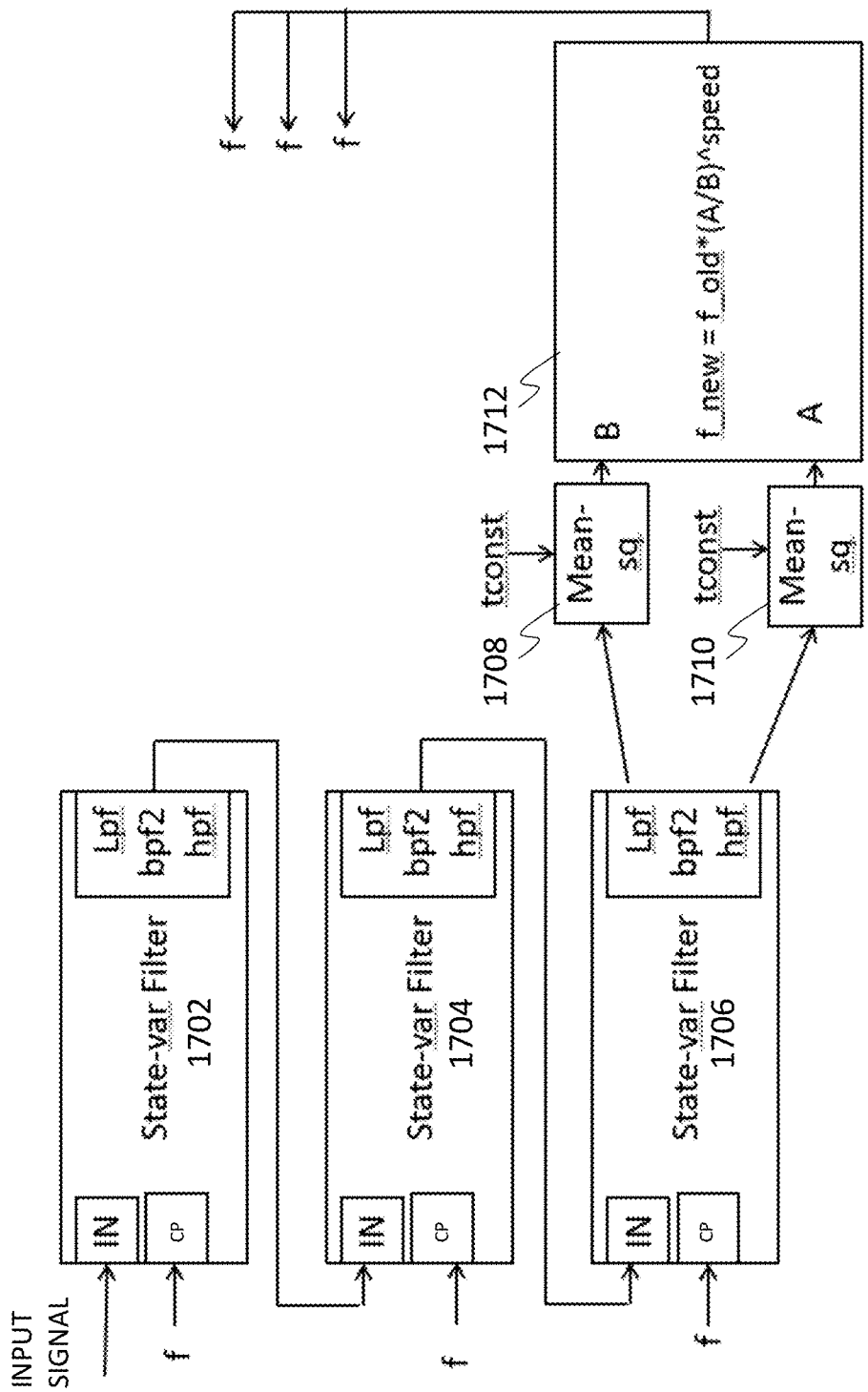
FIG. 17 illustrates an overall diagram of a tracking algorithm, according to some embodiments of the disclosure.

FIG. 17 illustrates an overall diagram of an exemplary tracking algorithm, according to some embodiments of the disclosure, where three state-variable filters 1702, 1704, and 1706, such as e.g. a Chamberlin filter, are cascaded. For each of these filters, in FIG. 17, "Lpf" refers to a low-pass output (e.g. output 1502 in FIG. 15), "hpf" refers to a high-pass output (e.g. output 1504 in FIG. 15), "bpf2" refers to a modified band-pass filter response as described below, "IN" refers to the input signal to the filter, and "CP" refers to one or more input control parameters (hence, CP) (for the case of Chamberlin filter as shown in FIG. 15, the control parameter being the parameter "f", as shown in FIG. 17 with "f" being provided to "CP").

Figure 18:
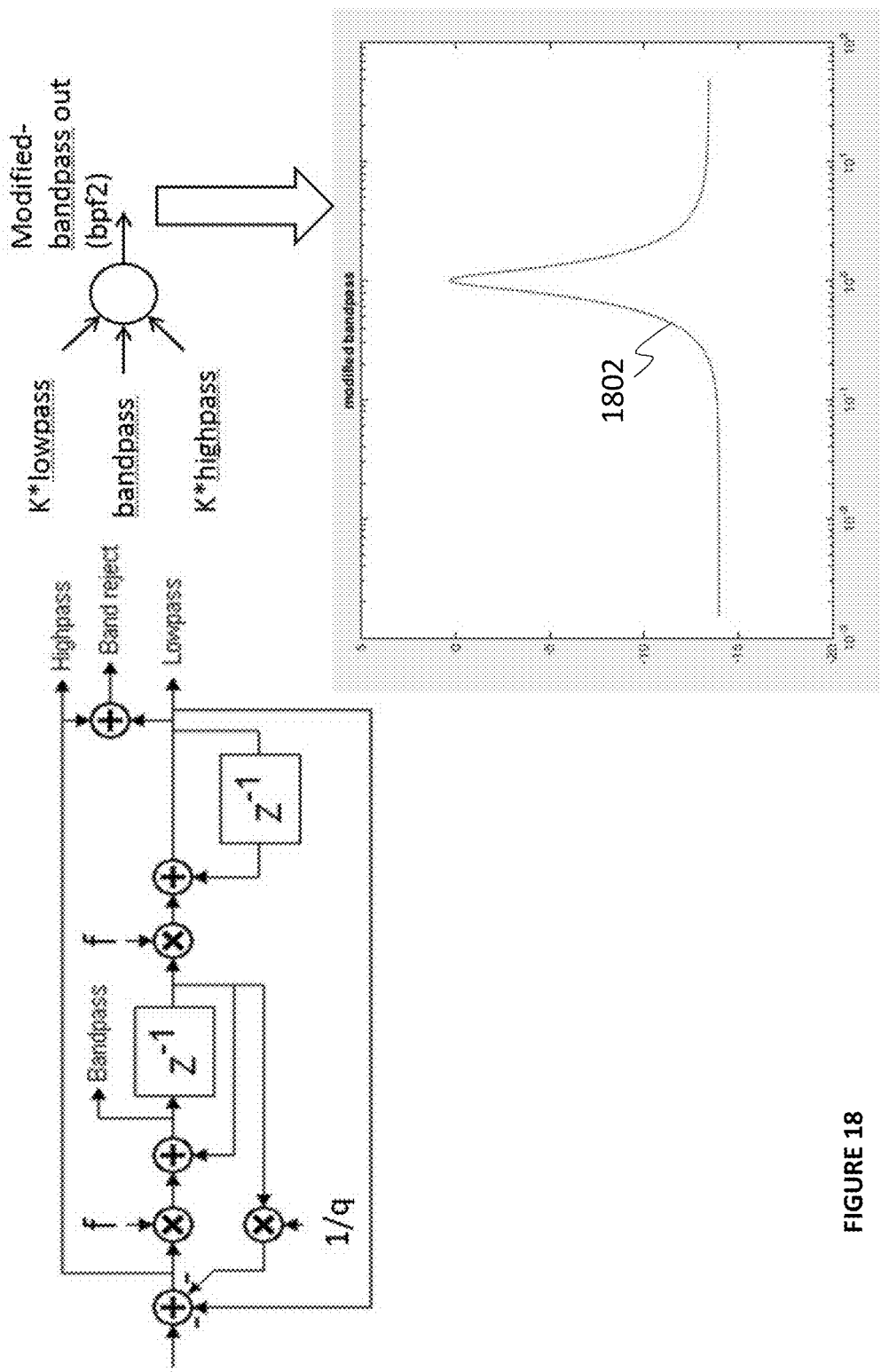
FIG. 18 illustrates a modified band-pass filter response, according to some embodiments of the disclosure.

FIG. 18 illustrates a modified band-pass filter response, according to some embodiments of the disclosure. As shown in FIG. 18, by adding a fraction (denoted in the FIGURE with a weight K) of the output of a high-pass filter and a fraction (also denoted in the FIGURE with a weight K, although these two weights could be different) of the output of a low-pass filter to a band-pass of the Chamberlin filter of FIG. 15, attenuation away from the peak may be limited, resulting in a state-variable filter with modified band-pass output (denoted as "bpf2"), as shown with a response 1802.

Turning back to the architecture of FIG. 17, since the filters 1702-1706 are cascaded to ensure a more pronounced peak, the filter 1702 receives the input signal (e.g. PPG signal) as an input, and then modified band-pass output "bpf2" of the filter 1702 is provided as an input signal to the filter 1704, while modified band-pass output "bpf2" of the filter 1704 is provided as an input signal to the filter 1706 (as shown in FIG. 17 with arrows between the corresponding parts). Then, amplitudes of the low-pass and high-pass outputs of the filter 1706 are determined as shown with boxes 1708 and 1710 and the control parameter f is updated accordingly (box 1712).

In FIG. 17, "A" refers to the mean square value of the outcome of the high-pass filter of the filter 1706, while "B" refers to the mean square value of the outcome of the low-pass filter of the filter 1706. However, in other embodiments, any other arbitrary function (besides the mean square value) that estimates amplitude of a response may be used.

Furthermore, in FIG. 17, the control parameter f is shown to be updated according to equation $$f_{new} = f_{old} * \left(\frac{A}{B}\right)^{speed},$$

indicating that the amplitudes of the first and second filters are evaluated in terms of their ratio (target ratio is 1), where $f_{old}$ and $f_{new}$ refer to the values of the control parameter f before and after the update, respectively, and speed refers to how rapidly the feedback system will respond to a rapidly-changing input frequency.

However, in other embodiments, updates may be performed differently. For example, the amplitudes of the first and second filters may be compared by considering their difference, in which case an update equation could be of the form:

$$f_{new} = f_{old} + \text{alpha} * (A-B),$$

where alpha refers to a positive value that controls how quickly the system responds to a difference between A and B. Both of such update equations shift the value of frequency F_RES (i.e., the frequency at which the amplitudes of the low-pass and high-pass outputs are equal) up when a high-pass output A is greater than a low-pass output B (in accordance with the right plot in FIG. 14) and down when a high-pass output A is less than a low-pass output B (in accordance with the left plot in FIG. 14), and would stop the first and second filters from adapting further when A=B, but the dynamics of how the low-pass and high-pass filters get there (i.e. how their control parameters change) may be somewhat different.

Other update equations that compare the outputs of the first and second filter and update the control parameters accordingly would be obvious to a person skilled in the art based on this description and, therefore, are within the scope of the present disclosure.

The updated value of the control parameter f is related to the resonant frequency F_RES by $$F\_RES = 2 * PI * f/fs$$

where fs is the sampling frequency and, in which case, control parameter f is the parameter used to set the integrator gains in the state-variable filter. Since the preferred update equation is only dependent on the ratio of A/B, it follows that any other variable that is linearly related to f could be updated instead, and the parameter f could then be calculated as a scaled version of that variable. For example, since F_RES and f are linearly related, the update equation could operate on a variable that was equivalent to F_RES, which could then be scaled by (fs/(2*PI)) to give the parameter f, which would then cause the state-variable filter to have a resonant frequency of F_RES. A person skilled in the art would recognize many other filter topologies that could achieve the same response shape, but may require a more complicated set of equations that produce multiple parameters in order to scale the frequency response of the filter appropriately, all of which are within the scope of the present disclosure.

Speed Vs Dampening of a Filter

As is well-known, damping of a filter is typically measured in terms of a quality factor referred to as "Q factor" or simply "Q." In order to be able to identify the resonant peaks where the amplitudes of the first and second filters are equal according to embodiments of the present disclosure, moderately high Q values are preferably used (otherwise the filter response is too wide and peaks are more difficult to identify). However, high Q values result in low speed and, consequently, a larger delay (lag) before a heart rate may be obtained. The delay may be unacceptably long, especially when the measurements are just beginning and it is important to get the first heart rate reading as soon as possible.

Figure 19:
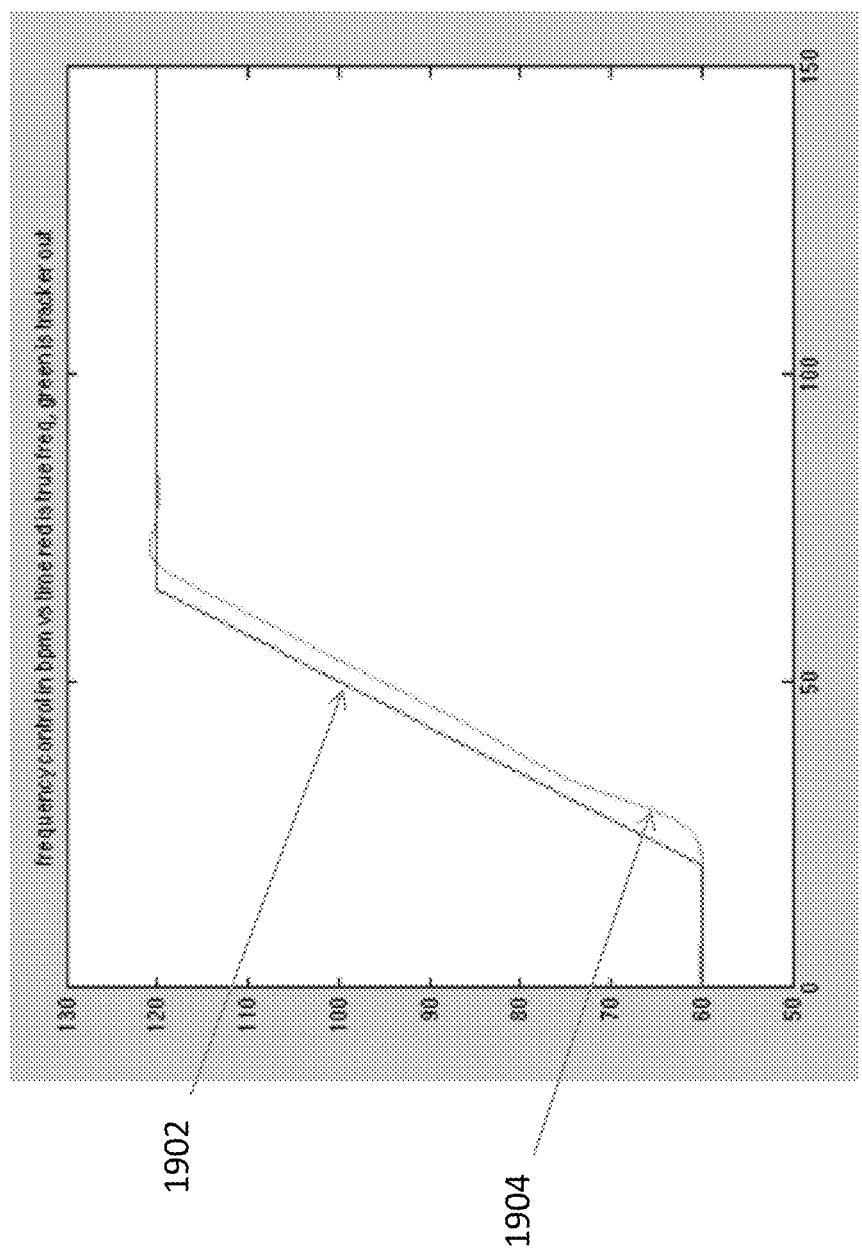
FIG. 19 illustrates track-speed for frequency-ramp input, according to some embodiments of the disclosure.

FIG. 19 illustrates track-speed for frequency-ramp input, according to some embodiments of the disclosure. In FIG. 19, line 1902 illustrates an instantaneous sinusoidal PPG input frequency produced artificially using standard formulas for producing frequency-modulated signals, and line 1904 illustrates a frequency identified as the frequency of the heartbeat signal by the tracker described herein. To generate the plots of FIG. 21, the worst-case dbpm/dt was assumed to be 60 bpm over 45 seconds, based on published data. In FIG. 19, the tracking filter lags by 3 seconds or has an error at a given time of 5 bpm. In an embodiment, the tracker 1104/212 may be configured to correct the readout of the heartbeat frequency by estimating the slope, e.g. based on empirical data.

Figure 20:
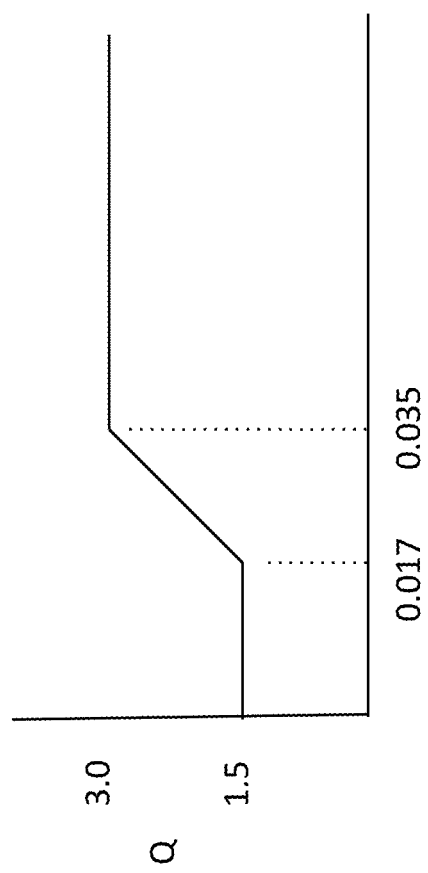
FIG. 20 illustrates tracking-filter dynamic modifications according to predicted interference, according to some embodiments of the disclosure.

In an embodiment, the Q factor of the first and/or second filters may be set based on the amount of motion present, e.g. based on a signal indicative of motion of the heart rate sensor during the acquisition of the input signal from which the heartbeat signal is being tracked, such as an accelerometer signal. This is illustrated in FIG. 20, where the y-axis is used to illustrate the Q values, while the x-axis is used to illustrate a parameter indicative of RMS values of all three accelerometer channels (total of all axes, accelerometer gains normalized to 1 G=1.0). For the simulation of FIG. 20, the variable "speed" was set to be equal to 0.001/Q.

When the accelerometer RMS magnitude (including all 3 axes) is below some threshold (i.e., there is relatively little motion), the motion artifacts in the PPG channel are minimal. In this case, the Q of the tracking filter can be lower, and the tracking speed can be higher (since speed is inversely proportional to Q), thus lowering the initial pulse acquisition time. When the accelerometer power is above some threshold, motion artifacts in the PPG signal begin to appear. In such a case, increasing the filter Q and decreasing the tracking speed allows the filter to robustly reject interfering signals. In this manner, the behavior of the tracking filter 1104/212 may be dynamically modified depending on the amount of motion.

It should be noted that FIG. 20 depicts adjustment of Q value based on empirical data, and, of course, in other embodiments the values depicted on the x- and y-axes may be different. In the example shown in FIG. 20, a value of 1.5 for the Q factor is considered a "low" value, while a value of 3.0 is considered a "high" value, the 0.017 and 0.035 values on the x-axis being the empirically derived thresholds where 1.0 represents 1 G of acceleration. FIG. 20 illustrates that, when accelerometer channels indicate that there is relatively little motion, e. g. as defined in terms of some predefined or dynamically defined first threshold (part of the graph for x being less than 0.017 in FIG. 19), low Q value may be used (i.e. high speed of adaptation). This is justified because with no or little motion, the input signal (e.g. PPG signal) is relatively clean (i.e. little, if any, motion-related artifacts) and the frequency on which the tracker 1104/212 locks on is likely to be the true heartbeat signal. FIG. 20 further illustrates that, as the amount of motion increases, e. g. as defined in terms of some predefined or dynamically defined second threshold (threshold in FIG. 20 being the x value greater than 0.035), Q may be increased. Higher Q means that then the speed is lower, but this sacrifice is justified because noisier data needs a sharper filter characteristic to robustly reject the noise and to extract the heartbeat frequency. Therefore, for x greater than 0.035, FIG. 20 illustrates that high Q value is used, with the Q value gradually increasing for x between 0.017 and 0.035.

Figure 21:
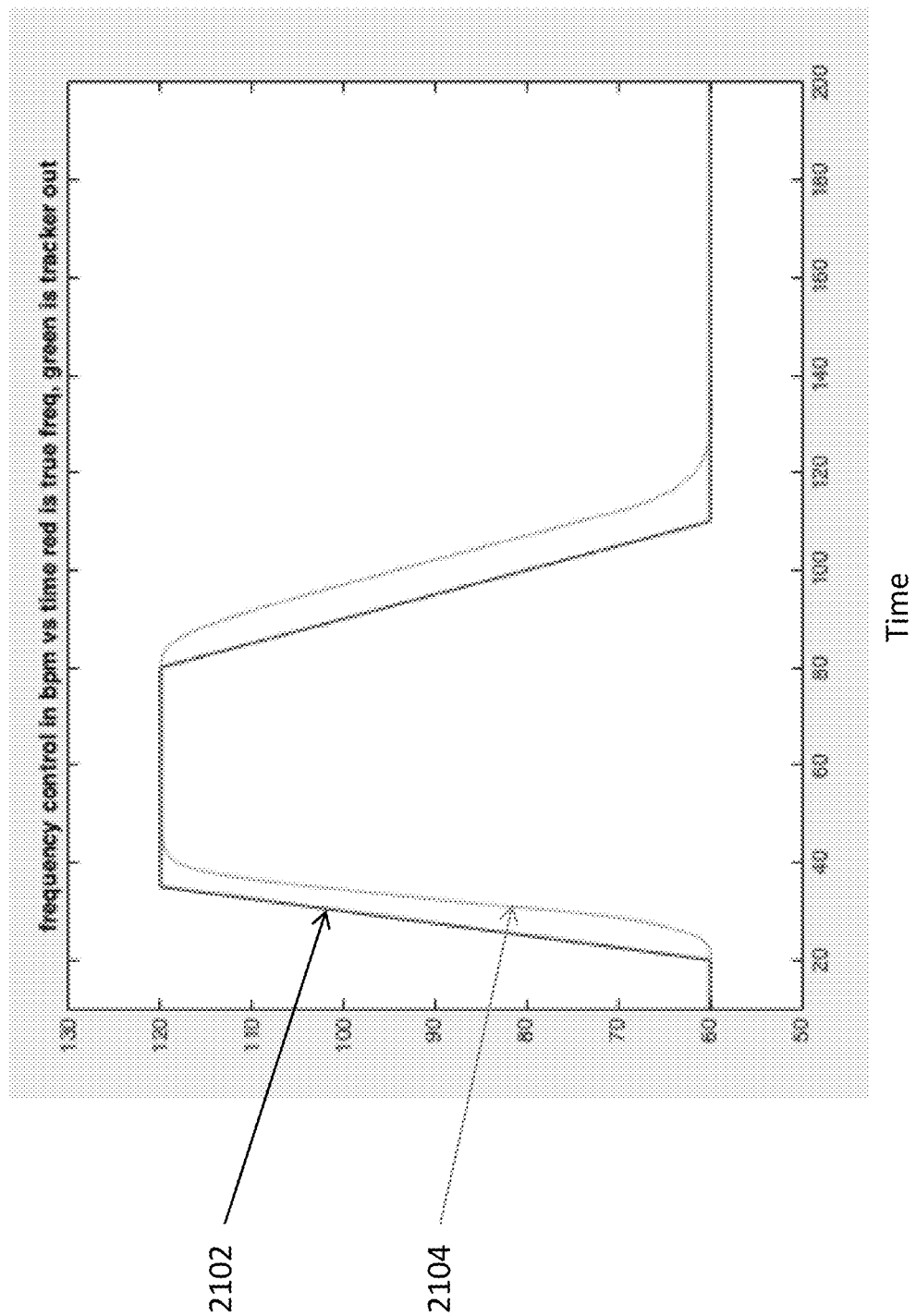
FIG. 21 illustrates tracking with asymmetric up/down time constants, according to some embodiments of the disclosure.

FIG. 21 illustrates an embodiment of tracking with asymmetric up/down time constants. In FIG. 21, line 2102 illustrates an instantaneous sinusoidal PPG input frequency, similar to the line 1902 of FIG. 19, and line 2104 illustrates a frequency identified as the frequency of the heartbeat signal within the PPG input by the tracker described herein, similar to the line 1904 of FIG. 19.

Measurements of heart-rates during real-life exercise sessions show that the maximum positive slew-rate of the heart rate (i.e. rate of change of heart-rate per unit of time) may be larger than a maximum negative heart rate slew-rate. To obtain the best tracking performance, it is desirable to match the asymmetric up/down rate of the input PPG signal by using asymmetric time constants in the filter update equation. New update equations may be formulated as:

Ratio=mean_sq(highpass)/mean_sq(lowpass)

If(ratio>1),speed=speed_nominal*(2*ratio−1)

else speed=speed_nominal

Fcontrol=Fcontrol*ratio^speed

Note that speed_nominal may be the Q-adjusted speed from FIG. 20.

If the asymmetric time constants are not used, then the overall tracking speed needs to be high enough to track the maximum observed positive slew rate in the PPG input data, and this leads to an overall sensitivity to noise in the input. This problem may be overcome by increasing the speed of the system when large positive slew-rates are encountered.

Simulation Results

Figure 22:
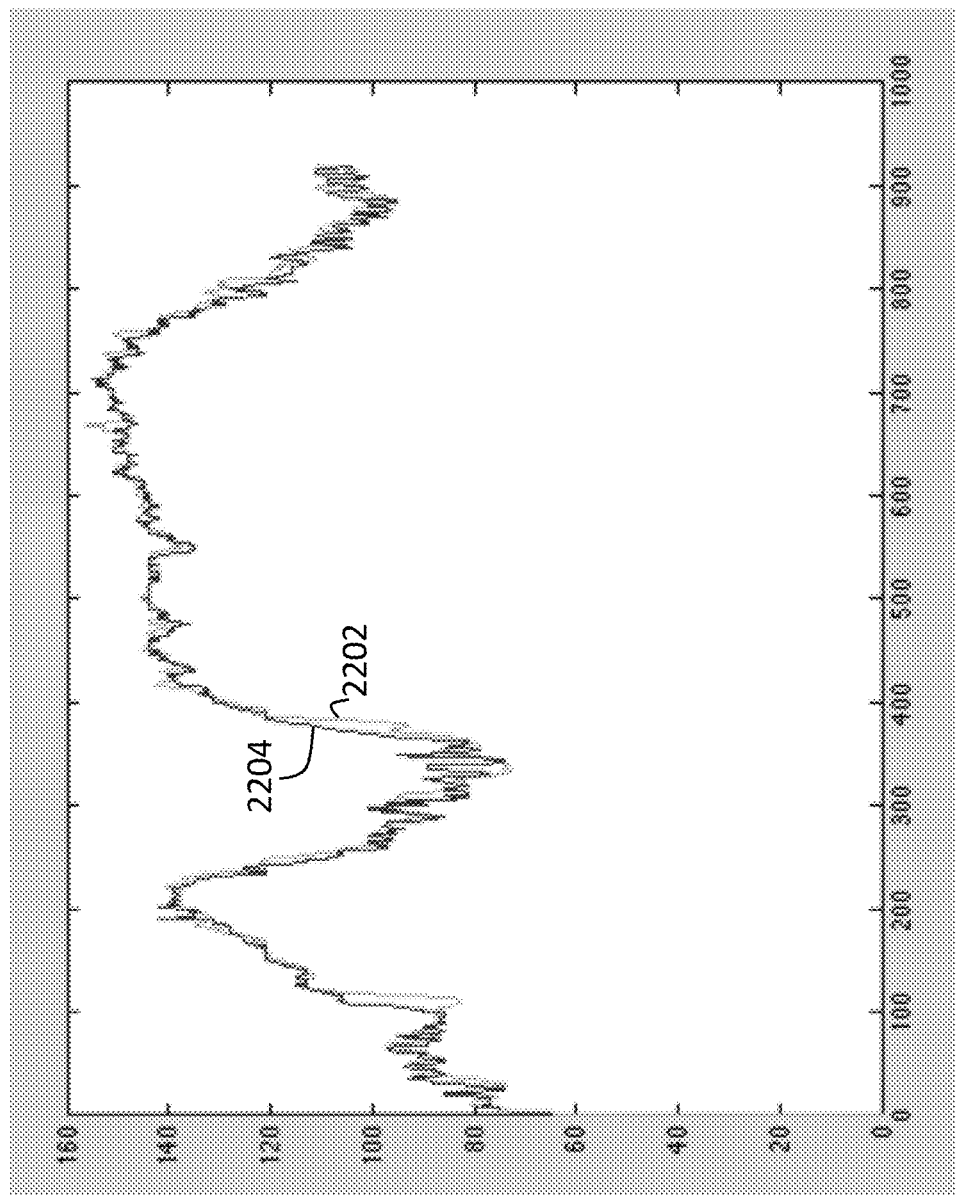
FIG. 22 illustrates comparison of heart rate monitoring during a 15-minute walk/jog/run using the time-domain interference removal according to the present disclosure and heart rate monitoring using electrocardiogram.

FIG. 22 illustrates comparison of heart rate monitoring during a 15-minute walk/jog/run using the time-domain interference removal with the tracking mechanism described herein (line 2202) and heart rate monitoring using electrocardiogram (ECG) (line 2204). The x-axis illustrates time, while the y-axis illustrates BPM. As illustrated in this FIGURE, implementing both the improved front-end as well as the improved back-end processing described herein enables highly accurate tracking of the frequency of a heartbeat signal.

EXAMPLES

Example 1A provides a method for assisting identification and/or tracking of a heartbeat signal present in one or more first signals generated by one or more sensors in a noisy environment, the method including steps of: receiving data samples of a first signal; receiving data samples of a second signal indicative of motion of the one or more sensors; applying adaptive linear prediction to at least a portion of data samples of the second signal to determine coefficients of an adaptive linear filter configured to filter at least a part of noise content present in the second signal from a signal indicative of the motion of the one or more sensors; and generating a filtered first signal by subtracting, from the first signal, a signal generated by applying, to the first signal, a filter including the determined coefficients.

Example 2A provides the method according to Example 1A, where the second signal includes at least a first portion indicative of motion of the one or more sensors with respect to a first direction and a second portion indicative of motion of the one or more sensors with respect to a second direction, and applying adaptive linear prediction to at least a portion of data samples of a second signal includes i) applying adaptive linear prediction to the first portion of the second signal to determine a first set of coefficients of a first adaptive linear filter configured to filter at least a part of noise content present in the first portion of the second signal from a signal indicative of the motion of the one or more sensors with respect to the first direction, and ii) applying adaptive linear prediction to the second portion of the second signal to determine a second set of coefficients of a second adaptive linear filter configured to filter at least a part of noise content present in the second portion of the second signal from a signal indicative of the motion of the one or more sensors with respect to the second direction.

Example 3A provides the method according to Example 2A, where generating a filtered first signal includes generating the filtered first signal by subtracting from the first signal a signal generated by applying a filter including the determined first set of coefficients to the first signal and subtracting a signal generated by applying a filter including the determined second set of coefficients to the first signal.

Example 4A provides the method according to any one of the preceding Examples, where the filter includes a finite impulse response (FIR) filter.

Example 5A provides the method according to any one of the preceding Examples, where the adaptive linear prediction is based on a power-normalized least mean square (LMS) update algorithm.

Example 6A provides the method according to any one of the preceding Examples, where an update equation of the power-normalized LMS algorithm includes a leak factor (LF).

Example 7A provides the method according to any one of the preceding Examples, further including processing the data samples of the second signal with a pre-processing filter to substantially attenuate signal content outside of a reasonable frequency band of interest corresponding to the heart beat before applying adaptive linear prediction.

Example 8A provides the method according to any one of the preceding Examples, where the pre-processing filter is a low-pass filter or a band-pass filter, and the reasonable frequency band of interest includes frequencies between 0.5 Hertz to 3.5 Hertz.

Example 9A provides the method according to any one of the preceding Examples, further including processing the data samples of the first signal with a pre-processing filter to substantially attenuate signal content outside of the reasonable frequency band of interest corresponding to the heart beat before generating the filtered first signal.

Example 10A provides the method according to Example 9A, where the pre-processing filter is a low-pass filter or a band-pass filter, and the reasonable frequency band of interest includes frequencies between 0.5 Hertz to 3.5 Hertz.

Example 11A provides the method according to any one of the preceding Examples, further including applying a filter or mask to or removing a portion of the data samples of the first signal indicative of a saturation condition of the one or more sensors prior to generating the filtered first signal.

Example 12A provides the method according to any one of the preceding Examples, further including applying a filter or mask to or removing a portion of the data samples of the second signal which is outside of an expected range of values for the second signal prior to applying adaptive linear prediction.

Example 13A provides the method according to any one of the preceding Examples, further including applying a filter or mask to or removing a portion of the data samples of the first signal which is outside of an expected range of values for the first signal prior to generating the filtered first signal.

Example 14A provides the method according to any one of the preceding Examples, further including processing the filtered first signal to track the heartbeat signal.

Example 15A provides the method according to Example 14A, where processing the filtered first signal to track the heartbeat signal includes generating a time-frequency representation of the filtered first signal, and tracking one or more contours present in the time-frequency representation to track the heartbeat signal.

Example 16A provides a system comprising means for implementing the method according to any one of Examples 1A-15A.

Example 17A provides a data structure for assisting implementation of the method according to any one of Examples 1A-15A.

Example 18A provides a system for assisting identification and/or tracking of a heartbeat signal present in one or more first signals generated by one or more sensors in a noisy environment, the system including at least one memory element configured to store computer executable instructions, and at least one processor coupled to the at least one memory element and configured, when executing the instructions, to carry out the method according to any one of Examples 1A-15A.

Example 19A provides the system according to Example 18A, further including the one or more sensors.

Example 20A provides the system according to Example 19A, where the one or more sensors include one or more of the following: optical sensor, audio sensor, capacitive sensor, magnetic sensor, chemical sensor, humidity sensor, moisture sensor, pressure sensor, and biosensor.

Example 21A provides the system according to any one of the preceding Examples, further comprising one or more accelerometers configured to generate the second signal.

Example 22A provides one or more non-transitory tangible media encoding logic that include instructions for execution that, when executed by a processor, are operable to perform operations for assisting identification and/or tracking of a heartbeat signal present in one or more first signals generated by one or more sensors in a noisy environment, the operations comprising operations of the method according to any one of Examples 1A-15A.

Example 1B provides a method for extracting a frequency of a heartbeat signal present within an input signal generated by one or more sensors using a structure configured to implement a first filter and a second filter, the first filter and the second filter being filters that have a frequency F_RES at which the amplitude of their outputs are substantially equal and for which, above the frequency F_RES, the amplitude of the first filter becomes larger than the amplitude of the second filter, and, below the frequency F_RES, the amplitude of the second filter becomes larger than the amplitude of the first filter, the method including steps of: a) determining an amplitude of an output generated by the first filter in response to the first filter receiving the input signal and one or more filter control parameters; b) determining an amplitude of an output generated by the second filter in response to the second filter receiving the input signal and the one or more filter control parameters; c) updating the filter control parameters based on the amplitudes of steps a) and b) and proceeding to step a); d) determining the frequency of the heartbeat signal based on the one or more filter control parameters.

Example 2B provides the method according to Example 1B, where the first filter and the second filter are filters of a Chamberlin state-variable filter.

Example 3B provides the method according to Examples 1B or 2B, further including adjusting the one or more filter control parameters based on a signal indicative of motion of the one or more sensors.

Example 4B provides the method according to Example 3B, where the adjustment of the one or more filter control parameters includes dynamically altering a Q factor of one or more $2^{nd}$-order IIR filters.

Example 5B provides the method according to any one of the preceding Examples, further including processing the input signal with a pre-processing filter to substantially attenuate signal content outside of a reasonable frequency band of interest corresponding to the heartbeat before performing step a).

Example 6B provides the method according to Example 5B, where the pre-processing filter is a low-pass filter or a band-pass filter; and the reasonable frequency band of interest includes frequencies between 0.5 Hertz to 3.5 Hertz.

Example 7B provides the method according to any one of the preceding Examples, where the input signal includes a filtered input signal and the method further includes generating the filtered input signal from a first signal generated by the one or more sensors, prior to steps a)-d), by applying adaptive linear prediction to at least a portion of data samples of a second signal, the second signal indicative of motion of the one or more sensors, to determine coefficients of an adaptive linear filter configured to filter at least a part of noise content present in the second signal from a signal indicative of the motion of the one or more sensors; and generating the filtered input signal by subtracting, from the first signal, a signal generated by applying, to the first signal, a filter including the determined coefficients.

Example 8B provides the method according to Example 7B, where the second signal includes at least a first portion indicative of motion of the one or more sensors with respect to a first direction and a second portion indicative of motion of the one or more sensors with respect to a second direction, and applying adaptive linear prediction to at least a portion of data samples of a second signal includes: i) applying adaptive linear prediction to the first portion of the second signal to determine a first set of coefficients of a first adaptive linear filter configured to filter at least a part of noise content present in the first portion of the second signal from a signal indicative of the motion of the one or more sensors with respect to the first direction, and ii) applying adaptive linear prediction to the second portion of the second signal to determine a second set of coefficients of a second adaptive linear filter configured to filter at least a part of noise content present in the second portion of the second signal from a signal indicative of the motion of the one or more sensors with respect to the second direction.

Example 9B provides the method according to Example 7B, where the adaptive linear prediction is based on a power-normalized least mean square (LMS) update algorithm.

Example 10B provides a heart rate monitoring system including a filter structure and one or more processing units. The filter structure is for enabling determination of a frequency of a heartbeat signal present within an input signal generated by one or more sensors, the filter structure configured to implement a first filter and a second filter, the first filter and the second filter being filters that have a frequency F_RES at which the amplitude of their outputs are substantially equal and for which, above the frequency F_RES, the amplitude of the first filter becomes larger than the amplitude of the second filter, and, below the frequency F_RES, the amplitude of the second filter becomes larger than the amplitude of the first filter. The one or more processing units are configured to: a) determine an amplitude of an output generated by the first filter in response to the first filter receiving the input signal and one or more filter control parameters; b) determine an amplitude of an output generated by the second filter in response to the second filter receiving the input signal and the one or more filter control parameters; c) update the filter control parameters based on the amplitudes of steps a) and b) and proceed to step a); and d) determine the frequency of the heartbeat signal based on the one or more filter control parameters.

Example 11B provides the heart rate monitoring system according to Example 10B, where the filter structure includes a Chamberlin state-variable filter.

Example 12B provides the heart rate monitoring system according to Examples 10B or 11B, where the filter structure includes one or more digital Infinite Input Response (IIR) filters, and the one or more filter control parameters control coefficients of the one or more digital IIR filters.

Example 13B provides the heart rate monitoring system according to any one of Examples 10B-12B, where the filter structure includes one or more digital Finite Input Response (FIR) filters, and the one or more filter control parameters control coefficients of the one or more digital FIR filters.

Example 14B provides the heart rate monitoring system according to any one of Examples 10B-13B, where the one or more processors are further configured to adjust the one or more filter control parameters based on a signal indicative of motion of the one or more sensors.

Example 15B provides the heart rate monitoring system according to Example 14B, where the filter structure includes one or more $2^{nd}$-order IIR filters, and the one or more processors are configured to adjust the one or more filter control parameters by dynamically altering a Q factor of the one or more $2^{nd}$-order IIR filters.

Example 16B provides the heart rate monitoring system according to any one of Examples 10B-15B, further including the one or more sensors.

Example 17B provides the heart rate monitoring system according to Example 16B, where the one or more sensors include one or more of the following: optical sensor, audio sensor, capacitive sensor, magnetic sensor, chemical sensor, humidity sensor, moisture sensor, pressure sensor, and biosensor.

Example 18B provides the heart rate monitoring system according to any one of Examples 10B-17B, further including a pre-processing filter configured to process the input signal to substantially attenuate signal content outside of a reasonable frequency band of interest corresponding to the heartbeat.

Example 19B provides the heart rate monitoring system according to Example 18B, where the pre-processing filter is a low-pass filter or a band-pass filter; and the reasonable frequency band of interest includes frequencies between 0.5 Hertz to 3.5 Hertz.

Example 20B provides the heart rate monitoring system according to any one of Examples 10B-19B, further including a filter configured to filter, prior to the one or more processing units performing steps a)-d), the input signal generated by the one or more sensors based on an accelerometer signal indicative of motion of the one or more sensors.

Example 21B provides a system comprising means for implementing the method according to any one of Examples 1B-9B.

Example 22B provides a data structure for assisting implementation of the method according to any one of Examples 1B-9B.

Example 23B provides one or more non-transitory tangible media encoding logic that include instructions for execution that, when executed by a processor, are operable to perform operations for assisting identification and/or tracking of a heartbeat signal present in one or more first signals generated by one or more sensors in a noisy environment, the operations comprising operations of the method according to any one of Examples 1B-9B.

The output of performing the method according to any one of Examples 1A-15A may serve as an input, possibly with further modifications, to the method according to any one of Examples 1B-9B. In other words, the filtered first signal generated as a result of performing a method according to any one of Examples 1A-15A may serve as a basis for the input signal, or be such an input signal, provided to the structure configured to implement the first filter and the second filter in performing a method according to any one of Examples 1B-9B.

Variations and Implementations

It is envisioned that a heart rate monitoring apparatus as described herein (which may include improved front-end processing without improved back-end processing described herein, or only improved back-end processing without improved front-end processing described herein, or both improved front-end and improved back-end processing) can be provided in many areas including medical equipment, security monitoring, patient monitoring, healthcare equipment, medical equipment, automotive equipment, aerospace equipment, consumer electronics, and sports equipment, etc.

In some cases, the heart rate monitoring apparatus can be used in professional medical equipment in a healthcare setting such as doctor's offices, emergency rooms, hospitals, etc. In some cases, the heart rate monitoring apparatus can be used in less formal settings, such as schools, gyms, homes, offices, outdoors, under water, etc. The heart rate monitoring apparatus can be provided in a consumer healthcare product.

The heart rate monitoring apparatus or parts thereof can take many different forms. Examples include watches, rings, wristbands, chest straps, headbands, headphones, ear buds, clamps, clips, clothing, bags, shoes, glasses, googles, hats, suits, necklace, attachments/patches/strips/pads which can adhere to a living being, accessories, portable devices, and so on. In particular, wearables technology (or referred often as "wearables", i.e., electronics which are intended to be worn by humans or other living beings) can greatly leverage the benefits of the heart rate monitoring apparatus disclosed herein due to the wearables' portability and the heart rate monitoring technique's robustness against motion artifacts. Even in the presence of noise, the wearable can effectively track a heart rate. Besides wearables, portable or mobile devices such as mobile phones and tablets can also include a processor having the tracking functions, an analog front end, a light source and a light sensor (or an extension (wired or wireless) having the light source and light sensor) to provide a heart rate monitoring apparatus. Users can advantageously use a ubiquitous mobile phone to make a heart rate measurement. Furthermore, it is envisioned that the heart rate monitoring apparatus can be used in wired or wireless accessories such as cuffs, clips, straps, bands, probes, etc., to sense physiological parameters of a living being. These accessories can be connected to a machine configured to provide the processor and the analog front end. The analog front end could be provided in the accessory or in the machine.

Besides tracking a heart rate, the heart rate monitoring apparatus can be provided to sense or measure other physiological parameters such as oxygen saturation (SpO2), blood pressure, respiratory rate, activity or movement, etc. Besides humans, the heart rate monitoring apparatus can be provided to measure slow tracking frequencies present in signals sensing other living beings such as animals, insects, plants, fungi, etc.

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure. For instance, instead of processing the signals in the digital domain, it is possible to provide equivalent electronics that can process the signals in the analog domain.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities. In some cases, application specific hardware can be provided with or in the processor to carry out those functionalities.

In another example embodiment, the electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the slow varying frequency tracking functionalities may be implemented in one or more silicon cores in Application Specific Integrated Circuits (ASICs), Field Programmable Gate Arrays (FPGAs), and other semiconductor chips.

Note that the activities discussed above with reference to the FIGURES are applicable to any integrated circuits that involve signal processing, particularly those that can execute specialized software programs, or algorithms, some of which may be associated with processing digitized real-time data to track a heart rate. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include pulmonary monitors, heart rate monitors, pacemakers, etc. Other applications can involve automotive technologies for safety systems (e.g., stability control systems, driver assistance systems, braking systems, infotainment and interior applications of any kind). Furthermore, powertrain systems (for example, in hybrid and electric vehicles) can use high-precision data conversion products in battery monitoring, control systems, reporting controls, maintenance activities, etc. It is envisioned that these applications can also utilize the disclosed improved method for tracking a slow moving frequency (e.g., tracking systems which are dampened to move at a frequency that changes slowly). In yet other example scenarios, the teachings of the present disclosure can be applicable in the industrial markets that include process control systems aiming to track a slow moving frequency to help drive productivity, energy efficiency, and reliability.

Note that with the numerous examples provided herein, interaction may be described in terms of two, three, four, or more parts. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the features of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, parts, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to tracking a slow varying frequency, illustrate only some of the possible tracking functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

Although the claims are presented in single dependency format in the style used before the USPTO, it should be understood that any claim can depend on and be combined with any preceding claim of the same type unless that is clearly technically infeasible.

Note that all optional features of the apparatus described above may also be implemented with respect to the method or process described herein and specifics in the examples may be used anywhere in one or more embodiments.

What is claimed is:

1. An apparatus for assisting identification and/or tracking of a heartbeat signal, the apparatus comprising:
    means for receiving, at one or more processing units, a first signal generated by at least one heartbeat sensor and a second signal generated by at least one motion sensor, the second signal indicative of a motion of the heartbeat sensor;
    means for applying, by the one or more processing units, adaptive linear prediction to at least a portion of the second signal to determine coefficients of an adaptive linear prediction filter configured to filter at least a part of noise content present in the second signal from a signal indicative of the motion of the heartbeat sensor; and
    means for generating, by the one or more processing units, a filtered first signal by subtracting, from the first signal, a signal generated by applying, to the first signal, a filter with the determined coefficients.

2. The apparatus according to claim 1, wherein:
    the second signal comprises at least a first portion indicative of motion of the heartbeat sensor with respect to a first direction and a second portion indicative of motion of the heartbeat sensor with respect to a second direction, and
    applying adaptive linear prediction to at least a portion of the second signal comprises:
        applying adaptive linear prediction to the first portion of the second signal to determine a first set of coefficients of a first adaptive linear prediction filter configured to filter at least a part of noise content present in the first portion of the second signal from a signal indicative of the motion of the heartbeat sensor with respect to the first direction, and
        applying adaptive linear prediction to the second portion of the second signal to determine a second set of coefficients of a second adaptive linear prediction filter configured to filter at least a part of noise content present in the second portion of the second signal from a signal indicative of the motion of the heartbeat sensor with respect to the second direction.

3. The apparatus according to claim 2, wherein generating a filtered first signal comprises generating the filtered first signal by subtracting from the first signal a signal generated by applying a filter with the determined first set of coefficients to the first signal and subtracting a signal generated by applying a filter with the determined second set of coefficients to the first signal.

4. The apparatus according to claim 1, wherein the filter comprises a finite impulse response (FIR) filter.

5. The apparatus according to claim 1, wherein the adaptive linear prediction is based on a power-normalized least mean square (LMS) update algorithm.

6. The apparatus according to claim 5, wherein an update equation of the power-normalized LMS update algorithm includes a leak factor (LF).

7. The apparatus according to claim 1, further comprising:
    means for processing the second signal with a pre-processing filter to substantially attenuate signal content outside of a reasonable frequency band of interest corresponding to the heartbeat before applying adaptive linear prediction.

8. The apparatus according to claim 1, further comprising:
    means for processing the first signal with a pre-processing filter to substantially attenuate signal content outside of the reasonable frequency band of interest corresponding to the heartbeat before generating the filtered first signal.

9. The apparatus according to claim 1, further comprising:
    means for applying a filter or mask to or removing a portion of data samples of the first signal indicative of a saturation condition of the heartbeat sensor prior to generating the filtered first signal.

10. The apparatus according to claim 1, further comprising:
    means for applying a filter or mask to or removing a portion of data samples of the second signal which is outside of an expected range of values for the second signal prior to applying adaptive linear prediction.

11. The apparatus according to claim 1, further comprising:

means for applying a filter or mask to or removing a portion of data samples of the first signal which is outside of an expected range of values for the first signal prior to generating the filtered first signal.

12. The apparatus according to claim 1, further comprising:
means for processing the filtered first signal to track the heartbeat signal.

13. An apparatus for assisting identification and/or tracking of a heartbeat signal, the apparatus comprising:
at least one heartbeat sensor configured to generate a first signal, the first signal indicative of the heartbeat signal;
one or more processing units configured to:
receive a second signal generated by at least one motion sensor, the second signal indicative of a motion of the heartbeat sensor, and
apply adaptive linear prediction to at least a portion of the second signal to determine coefficients of an adaptive linear prediction filter configured to filter at least a part of noise content present in the second signal from a signal indicative of the motion of the heartbeat sensor; and
a filter structure configured to implement a filter for generating a filtered first signal by subtracting, from the first signal, a signal generated by applying to the first signal a filter with the determined coefficients.

14. The apparatus according to claim 13, wherein the heartbeat sensor includes one or more of the following: optical sensor, audio sensor, capacitive sensor, magnetic sensor, chemical sensor, humidity sensor, moisture sensor, pressure sensor, and biosensor.

15. The apparatus according to claim 13, further comprising the motion sensor.

16. A non-transitory computer readable storage medium storing software code portions configured for, when executed on a processor, carrying out a method for assisting identification and/or tracking of a heartbeat signal, the method comprising:
receiving, at one or more processing units, a first signal generated by at least one heartbeat sensor and a second signal generated by at least one motion sensor, the second signal indicative of a motion of the heartbeat sensor;
applying, by the one or more processing units, adaptive linear prediction to at least a portion of the second signal to determine coefficients of an adaptive linear prediction filter configured to filter at least a part of noise content present in the second signal from a signal indicative of the motion of the heartbeat sensor; and
generating, by the one or more processing units, a filtered first signal by subtracting, from the first signal, a signal generated by applying, to the first signal, a filter with the determined coefficients.

17. The non-transitory computer readable storage medium according to claim 16, wherein:
the second signal comprises at least a first portion indicative of motion of the heartbeat sensor with respect to a first direction and a second portion indicative of motion of the heartbeat sensor with respect to a second direction, and
applying adaptive linear prediction to at least a portion of the second signal comprises:
applying adaptive linear prediction to the first portion of the second signal to determine a first set of coefficients of a first adaptive linear prediction filter configured to filter at least a part of noise content present in the first portion of the second signal from a signal indicative of the motion of the heartbeat sensor with respect to the first direction, and
applying adaptive linear prediction to the second portion of the second signal to determine a second set of coefficients of a second adaptive linear prediction filter configured to filter at least a part of noise content present in the second portion of the second signal from a signal indicative of the motion of the heartbeat sensor with respect to the second direction.

18. The non-transitory computer readable storage medium according to claim 17, wherein generating a filtered first signal comprises generating the filtered first signal by subtracting from the first signal a signal generated by applying a filter with the determined first set of coefficients to the first signal and subtracting a signal generated by applying a filter with the determined second set of coefficients to the first signal.

19. The apparatus according to claim 1, wherein the apparatus is a wearable or a portable apparatus.

* * * * *